(12) United States Patent
Griffin et al.

(10) Patent No.: US 12,351,644 B2
(45) Date of Patent: *Jul. 8, 2025

(54) ANTI-CD73 ANTIBODIES

(71) Applicant: CORVUS PHARMACEUTICALS, INC., Burlingame, CA (US)

(72) Inventors: Emily Piccione Griffin, Belmont, CA (US); Richard A. Miller, Portola Valley, CA (US); Ian McCaffery, Oakland, CA (US)

(73) Assignee: Corvus Pharmaceuticals, Inc., Burlingame, CA (US)

( * ) Notice: Subject to any disclaimer, the term of this patent is extended or adjusted under 35 U.S.C. 154(b) by 907 days.

This patent is subject to a terminal disclaimer.

(21) Appl. No.: 17/005,051

(22) Filed: Aug. 27, 2020

(65) Prior Publication Data

US 2021/0221905 A1 Jul. 22, 2021

Related U.S. Application Data

(63) Continuation of application No. 15/647,212, filed on Jul. 11, 2017, now Pat. No. 10,793,636.

(60) Provisional application No. 62/395,875, filed on Sep. 16, 2016, provisional application No. 62/360,804, filed on Jul. 11, 2016.

(51) Int. Cl.
*A61K 39/00* (2006.01)
*A61P 35/00* (2006.01)
*C07K 16/28* (2006.01)

(52) U.S. Cl.
CPC .......... *C07K 16/2896* (2013.01); *A61P 35/00* (2018.01); *A61K 2039/505* (2013.01); *C07K 2317/24* (2013.01); *C07K 2317/41* (2013.01); *C07K 2317/565* (2013.01); *C07K 2317/76* (2013.01); *C07K 2317/92* (2013.01); *C07K 2317/94* (2013.01)

(58) Field of Classification Search
CPC .............................................. A61K 2039/505
See application file for complete search history.

(56) References Cited

U.S. PATENT DOCUMENTS

| 5,530,101 | A | 6/1996 | Queen et al. |
| 6,881,557 | B2 | 4/2005 | Foote |
| 8,354,415 | B2 | 1/2013 | Jordan et al. |
| 8,450,328 | B2 | 5/2013 | Bamford et al. |
| 9,120,807 | B2 | 9/2015 | Jordan et al. |
| 2014/0235833 | A1 | 8/2014 | Sugioka et al. |
| 2016/0129108 | A1 | 5/2016 | Sachsenmeier et al. |
| 2018/0237536 | A1 | 8/2018 | Perrot et al. |
| 2019/0055320 | A1 | 2/2019 | Lonberg et al. |
| 2019/0077873 | A1* | 3/2019 | Griffin ............... C07K 16/2896 |

FOREIGN PATENT DOCUMENTS

| WO | WO-2017/100670 A1 | 6/2017 |
| WO | WO-2017/118613 A1 | 7/2017 |
| WO | WO-2017/197331 A2 | 11/2017 |
| WO | WO-2018/187512 A1 | 10/2018 |

OTHER PUBLICATIONS

Antonioli, Luca, et al., "Anti-CD73 in cancer immunotherapy: awakening new opportunities." Trends in cancer 2.2 (2016): 95-109.
Mariuzza et al. (Annu. Rev. Biophys. Biophys. Chem. 1987; 16: 139-159).
Piccione, et al. (2017), "A novel CD73-blocking antibody reduces production of immunosuppressive adenosine and restores T cell function." Cancer Research; 77(13 Suppl): Abstract 5577. 3 pages. In: Proceedings of the American Association for Cancer Research Annual Meeting 2017; Apr. 1-5, 2017; Washington, DC.
Rudikoff et al. (Proc. Natl. Acad. Sci. USA. 1982; 79: 1979-1983).
Stagg et al. (Proc. Natl. Acad. Sci. USA. Jan. 26, 2010; 107 (4): 1547-52).
Terp et al. (J. Immunol. Oct. 15, 2013; 191 (8): 4165-73).
Winkler et al. (J. Immunol. Oct. 15, 2000; 165 (8): 4505-4514).
Sachsenmeier, K. F. et al. (2012). "Development of a Novel Ectonucleotidase Assay Suitable for High-Throughput Screening." Journal of Biomolecular Screening, 17(7), 993-998. DOI 10.1177/1087057112443987 Retrieved from the Internet: URL:https:/dul.usage.elsevier.com/doi.

* cited by examiner

*Primary Examiner* — Stephen L Rawlings
(74) *Attorney, Agent, or Firm* — Mintz Levin Cohn Ferris Glovsky and Popeo, P.C.

(57) ABSTRACT

Provided herein are, inter alia, anti-CD73 antibodies and methods of using the same. The antibodies provided include amino acid substitution embodiments affecting the antibody glycosylation state. The antibodies provided herein are, inter alia, useful for the treatment of cancer and effective for inhibition of CD73 activity.

11 Claims, 5 Drawing Sheets
Specification includes a Sequence Listing.

Fig. 7
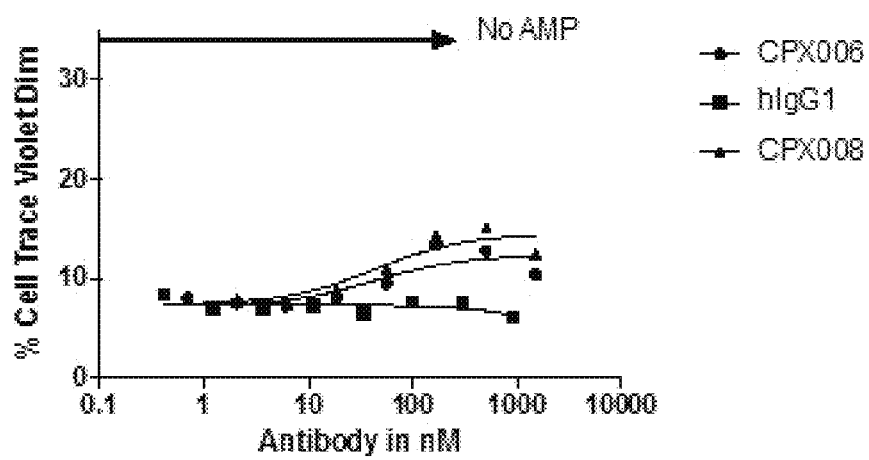
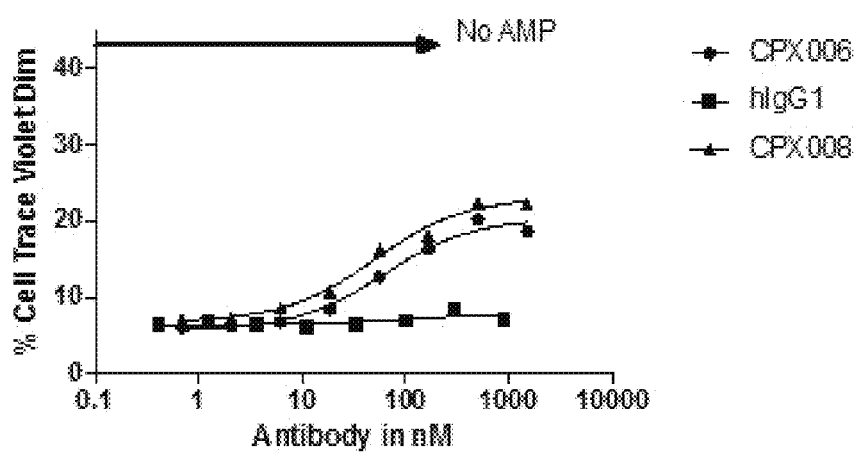

SEQUENCE LISTING

```
<160> NUMBER OF SEQ ID NOS: 28

<210> SEQ ID NO 1
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 1

Arg Ala Ser Lys Asn Val Ser Thr Ser Gly Tyr Ser Tyr Met His
```

```
<210> SEQ ID NO 2
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 2

Leu Ala Ser Asn Leu Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 3

Gln His Ser Arg Glu Leu Pro Phe Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 4

Gly Tyr Thr Phe Thr Ser Tyr Trp Ile Thr
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 5

Pro Gly Ser Gly Asn Thr Asn Tyr Asn Glu Lys Phe Lys Thr
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 6

Glu Gly Gly Leu Thr Thr Glu Asp Tyr
1               5

<210> SEQ ID NO 7
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 7

Ala Ile Gln Leu Thr Gln Ser Pro Ser Ser Leu Ser Ala Ser Val Gly
1               5                   10                  15
```

```
Asp Arg Val Thr Ile Thr Cys Arg Ala Ser Lys Asn Val Ser Thr Ser
                20                  25                  30

Gly Tyr Ser Tyr Met His Trp Tyr Gln Gln Lys Pro Gly Gln Ala Pro
            35                  40                  45

Arg Leu Leu Ile Tyr Leu Ala Ser Asn Leu Glu Ser Gly Val Pro Ser
        50                  55                  60

Arg Phe Ser Gly Ser Gly Ser Gly Thr Asp Phe Thr Phe Thr Ile Ser
65                  70                  75                  80

Ser Leu Glu Ala Glu Asp Ala Ala Thr Tyr Tyr Cys Gln His Ser Arg
                85                  90                  95

Glu Leu Pro Phe Thr Phe Gly Gln Gly Thr Lys Val Glu Ile Lys
            100                 105                 110
```

<210> SEQ ID NO 8
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 8

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Asn Val Ser Thr Ser
                20                  25                  30

Gly Tyr Ser Tyr Met His Trp Tyr Gln Gln Lys Pro Gly Gln Ala Pro
            35                  40                  45

Arg Leu Leu Ile Tyr Leu Ala Ser Asn Leu Glu Ser Gly Ile Pro Pro
        50                  55                  60

Arg Phe Ser Gly Ser Gly Tyr Gly Thr Asp Phe Thr Leu Thr Ile Asn
65                  70                  75                  80

Asn Ile Glu Ser Glu Asp Ala Ala Tyr Tyr Phe Cys Gln His Ser Arg
                85                  90                  95

Glu Leu Pro Phe Thr Phe Gly Gln Gly Thr Lys Val Glu Ile Lys
            100                 105                 110
```

<210> SEQ ID NO 9
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 9

```
Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Ser Tyr
                20                  25                  30

Trp Ile Thr Trp Val Arg Gln Ala Pro Gly Gln Gly Leu Glu Trp Met
            35                  40                  45

Gly Asp Ile Tyr Pro Gly Ser Gly Asn Thr Asn Tyr Asn Glu Lys Phe
        50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Glu Gly Gly Leu Thr Thr Glu Asp Tyr Ala Leu Asp Tyr Trp
```

```
              100                 105                 110
Gly Gln Gly Thr Leu Val Thr Val
        115                 120

<210> SEQ ID NO 10
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 10
gccatccagt tgacccagtc tccatcctcc ctgtctgcat ctgtaggaga cagagtcacc     60
atcacttgca gggccagcaa aaatgtcagt acatctggct atagttatat gcactggtac    120
cagcagaaac ctggccaggc tcccaggctc ctcatctatc ttgcatccaa cctagaatct    180
ggggtcccct cgaggttcag tggcagtgga tctgggacag atttcacctt taccatcagt    240
agcctggaag ctgaagatgc tgcaacatat tactgtcagc acagtaggga gcttccattc    300
acgttcggcc aagggaccaa ggtggaaatc aaa                                 333

<210> SEQ ID NO 11
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 11
gaaattgtgt tgacacagtc tccagccacc ctgtctttgt ctccagggga aagagccacc     60
ctctcctgca gggccagcaa aaatgtcagt acatctggct atagttatat gcactggtac    120
cagcagaaac ctggccaggc tcccaggctc ctcatctatc ttgcatccaa cctagaatct    180
gggatcccac ctcgattcag tggcagcggg tatggaacag attttaccct cacaattaat    240
aacatagaat ctgaggatgc tgcatattac ttctgtcagc acagtaggga gcttccattc    300
acgttcggcc aagggaccaa ggtggaaatc aaa                                 333

<210> SEQ ID NO 12
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 12
caggttcagc tggtgcagtc tggagctgag gtggagaagc ctggggcctc agtgaaggtc     60
tcctgcaagg cttctggcta caccttcacc agctactgga taacctgggt gcgacaggcc    120
cctggacaag gcttgagtg gatgggtgat atttatcctg gtagtggtaa tactaactac    180
aatgagaagt tcaagaccag agtcacgatt accgcggaca atccacgag cacagcctac    240 atggagctga gcagcctgag atctgaggac acggccgtgt attactgtgc aaaagaggga    300
ggtcttacta cggaggatta tgctttggac tactggggcc agggaacgct ggtcaccgtc    360
agctca                                                               366

<210> SEQ ID NO 13
<211> LENGTH: 218
<212> TYPE: PRT
<213> ORGANISM: Artificial Sequence
<220> FEATURE:
```

<223> OTHER INFORMATION: Synthetic polypeptide

<400> SEQUENCE: 13

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Asn Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Ile Pro Pro
    50                  55                  60

Arg Phe Ser Gly Ser Gly Tyr Gly Thr Asp Phe Thr Leu Thr Ile Asn
65                  70                  75                  80

Asn Ile Glu Ser Glu Asp Ala Ala Tyr Tyr Phe Cys Gln His Ser Arg
                85                  90                  95

Glu Leu Pro Phe Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 14
<211> LENGTH: 452
<212> TYPE: PRT
<213> ORGANISM: Artificial Sequence
<220> FEATURE:
<223> OTHER INFORMATION: Synthetic polypeptide

<400> SEQUENCE: 14

```
Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Ser Tyr
            20                  25                  30

Trp Ile Thr Trp Val Arg Gln Ala Pro Gly Gln Gly Leu Glu Trp Met
        35                  40                  45

Gly Asp Ile Tyr Pro Gly Ser Gly Asn Thr Asn Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Glu Gly Gly Leu Thr Thr Glu Asp Tyr Ala Leu Asp Tyr Trp
            100                 105                 110

Gly Gln Gly Thr Leu Val Thr Val Ser Ser Ala Ser Thr Lys Gly Pro
        115                 120                 125
```

```
Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Gln Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 15
<211> LENGTH: 218
<212> TYPE: PRT
<213> ORGANISM: Artificial Sequence
<220> FEATURE:
<223> OTHER INFORMATION: Synthetic polypeptide

<400> SEQUENCE: 15

Ala Ile Gln Leu Thr Gln Ser Pro Ser Ser Leu Ser Ala Ser Val Gly
1               5                   10                  15

Asp Arg Val Thr Ile Thr Cys Arg Ala Ser Lys Asn Val Ser Thr Ser
            20                  25                  30
```

Gly Tyr Ser Tyr Met His Trp Tyr Gln Gln Lys Pro Gly Gln Ala Pro
            35                  40                  45

Arg Leu Leu Ile Tyr Leu Ala Ser Asn Leu Glu Ser Gly Val Pro Ser
 50                  55                  60

Arg Phe Ser Gly Ser Gly Ser Gly Thr Asp Phe Thr Phe Thr Ile Ser
65                  70                  75                  80

Ser Leu Glu Ala Glu Asp Ala Ala Thr Tyr Tyr Cys Gln His Ser Arg
                85                  90                  95

Glu Leu Pro Phe Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 16
<211> LENGTH: 452
<212> TYPE: PRT
<213> ORGANISM: Artificial Sequence
<220> FEATURE:
<223> OTHER INFORMATION: Synthetic polypeptide

<400> SEQUENCE: 16

Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Ser Tyr
            20                  25                  30

Trp Ile Thr Trp Val Arg Gln Ala Pro Gly Gln Gly Leu Glu Trp Met
            35                  40                  45

Gly Asp Ile Tyr Pro Gly Ser Gly Asn Thr Asn Tyr Asn Glu Lys Phe
 50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Glu Gly Gly Leu Thr Thr Glu Asp Tyr Ala Leu Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Leu Gly Thr Gln Thr Tyr Ile Cys Asn Val Asn
            195                 200                 205

His Lys Pro Ser Asn Thr Lys Val Asp Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Gln Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 17
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 17

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Asn Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Thr
    50                  55                  60

Arg Phe Ser Gly Ser Gly Ser Gly Thr Asp Phe Thr Leu Asn Ile His
65                  70                  75                  80

```
Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys
            100                 105                 110
```

<210> SEQ ID NO 18
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 18

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Trp Ile Thr Trp Val Lys Gln Arg Pro Gly Gln Gly Leu Glu Trp Ile
            35                  40                  45

Gly Asp Ile Tyr Pro Gly Ser Gly Asn Thr Asn Tyr Asn Glu Lys Phe
    50                  55                  60

Lys Thr Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Lys Glu Gly Gly Leu Thr Thr Glu Asp Tyr Ala Leu Asp Tyr Trp
            100                 105                 110

Gly Gln Gly Thr Leu Val Thr Val Ser Ser
            115                 120
```

<210> SEQ ID NO 19
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 19

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gln Val Ser Thr Ser
                20                  25                  30

Gly Tyr Ser Tyr Met His Trp Tyr Gln Gln Lys Pro Gly Gln Ala Pro
            35                  40                  45

Arg Leu Leu Ile Tyr Leu Ala Ser Asn Leu Glu Ser Gly Ile Pro Pro
    50                  55                  60

Arg Phe Ser Gly Ser Gly Tyr Gly Thr Asp Phe Thr Leu Thr Ile Asn
65                  70                  75                  80

Asn Ile Glu Ser Glu Asp Ala Ala Tyr Tyr Phe Cys Gln His Ser Arg
                85                  90                  95

Glu Leu Pro Phe Thr Phe Gly Gln Gly Thr Lys Val Glu Ile Lys
            100                 105                 110
```

<210> SEQ ID NO 20
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 20

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ala Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Ile Pro Pro
    50                  55                  60

Arg Phe Ser Gly Ser Gly Tyr Gly Thr Asp Phe Thr Leu Thr Ile Asn
65                  70                  75                  80

Asn Ile Glu Ser Glu Asp Ala Ala Tyr Tyr Phe Cys Gln His Ser Arg
                85                  90                  95

Glu Leu Pro Phe Thr Phe Gly Gln Gly Thr Lys Val Glu Ile Lys
            100                 105                 110
```

<210> SEQ ID NO 21
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 21

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Asn Val Ala Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Ile Pro Pro
    50                  55                  60

Arg Phe Ser Gly Ser Gly Tyr Gly Thr Asp Phe Thr Leu Thr Ile Asn
65                  70                  75                  80

Asn Ile Glu Ser Glu Asp Ala Ala Tyr Tyr Phe Cys Gln His Ser Arg
                85                  90                  95

Glu Leu Pro Phe Thr Phe Gly Gln Gly Thr Lys Val Glu Ile Lys
            100                 105                 110
```

<210> SEQ ID NO 22
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 22

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Lys Gln Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Phe Thr Ile Ser
65                  70                  75                  80
```

```
Ser Leu Glu Ala Glu Asp Ala Ala Thr Tyr Tyr Cys Gln His Ser Arg
                85                  90                  95

Glu Leu Pro Phe Thr Phe Gly Gln Gly Thr Lys Val Glu Ile Lys
            100                 105                 110

<210> SEQ ID NO 23
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Asp Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Ile Pro Pro
    50                  55                  60

Arg Phe Ser Gly Ser Gly Tyr Gly Thr Asp Phe Thr Leu Thr Ile Asn
65                  70                  75                  80

Asn Ile Glu Ser Glu Asp Ala Ala Tyr Tyr Phe Cys Gln His Ser Arg
                85                  90                  95

Glu Leu Pro Phe Thr Phe Gly Gln Gly Thr Lys Val Glu Ile Lys
            100                 105                 110

<210> SEQ ID NO 24
<211> LENGTH: 1407
<212> TYPE: DNA
<213> ORGANISM: Artificial Sequence
<220> FEATURE:
<223> OTHER INFORMATION: Synthetic polynucleotide

<400> SEQUENCE: 24
atggggtcaa ccgccatcct tggcctcctc ctggctgttc tccaaggagt ctgtgcccag     60
gttcagctgg tgcagtctgg agctgaggtg agaagcctg gggcctcagt gaaggtctcc    120
tgcaaggctt ctggctacac cttcaccagc tactggataa cctgggtgcg acaggcccct    180 ggacaaggc ttgagtggat gggtgatatt tatcctggta gtggtaatac taactacaat    240
gagaagttca agaccagagt cacgattacc gcggacaaat ccacgagcac agcctacatg    300
gagctgagca gcctgagatc tgaggacacg gccgtgtatt actgtgcaaa agagggaggt    360
cttactacgg aggattatgc tttggactac tggggccagg gaacgctggt caccgtcagc    420
tcagctagca ccaagggccc atccgtcttc ccctggcgc cctgctccag gtctacctcc    480
gagtctacag ccgccctggg ctgcctggtc aaggactact ccccgaacc ggtgacggtg    540 tcgtggaact caggcgccct gacctctggc gtgcacacct tcccggctgt cctacagtcc    600
tcaggactct actccctctc ttctgtggtg accgtgccct cctcttcttt gggcacgaag    660
acctacacct gcaacgtaga tcacaagccc tctaacacca aggtggacaa gagagttgag    720
tccaaatatg gtcccccatg cccaccatgc ccagcacctg agttcctggg ggaccatca    780 gtcttcctgt tccccccaaa acccaaggac actctcatga tctcccggac ccctgaggtc    840
acgtgcgtgt ggtggacgt gtctcaggaa gaccccgagg tccagttcaa ctggtacgtg    900
gatggcgtgg aggtgcataa tgccaagaca aagccgcggg aggagcagtt caactctacg    960
```

```
taccgtgtgg tctctgtcct caccgtcctg caccaggact ggctgaacgg caaggagtac    1020
aagtgcaagg tctccaacaa aggcctcccg tcctccatcg agaaaaccat ctccaaagcc    1080
aaagggcagc cccgagagcc acaggtgtac accctgcccc catcccagga ggagatgacc    1140
aagaaccagg tctctctgac ctgcctggtc aaaggcttct acccctctga catcgccgtg    1200
gagtgggagt ctaatgggca gccggagaac aactacaaga ccacgcctcc cgtgctggac    1260
tccgacggct ccttcttcct ctactctagg ctaaccgtgg acaagtctag gtggcaggag    1320
gggaatgtct tctcatgctc cgtgatgcat gaggctctgc acaaccacta cacacagaag    1380
tctctctccc tgtctctggg taaatga                                        1407
```

<210> SEQ ID NO 25
<211> LENGTH: 717
<212> TYPE: DNA
<213> ORGANISM: Artificial Sequence
<220> FEATURE:
<223> OTHER INFORMATION: Synthetic polynucleotide

<400> SEQUENCE: 25

```
atggaagccc cagcgcagct tctcttcctc ctgctactct ggctcccaga taccaccgga     60
gaaattgtgt tgacacagtc tccagccacc ctgtctttgt ctccagggga agagccacc     120 ctctcctgca gggccagcaa acaggtcagt acatctggct atagttatat gcactggtac    180
cagcagaaac ctggccaggc tcccaggctc ctcatctatc ttgcatccaa cctagaatct    240
gggatcccac tcgattcag tggcagcggg tatggaacag attttaccct cacaattaat    300
aacatagaat ctgaggatgc tgcatattac ttctgtcagc acagtaggga gcttccattc    360
acgttcggcc aagggaccaa ggtggaaatc aaacgtacgg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc ctccaatcg    540 ggtaactccc aggagagtgt cacagagcag gactctaagg actctaccta ctctctctct    600
tctaccctga cgctgtctaa gcagactacg agaaacaca agtctacgc ctgcgaagtc    660 acccatcagg gcctgtcttc gcccgtcaca aagtctttca cagggagaga gtgttga     717
```

<210> SEQ ID NO 26
<211> LENGTH: 468
<212> TYPE: PRT
<213> ORGANISM: Artificial Sequence
<220> FEATURE:
<223> OTHER INFORMATION: Synthetic polypeptide

<400> SEQUENCE: 26

```
Met Gly Ser Thr Ala Ile Leu Gly Leu Leu Leu Ala Val Leu Gln Gly
1               5                   10                  15

Val Cys Ala Gln Val Gln Leu Val Gln Ser Gly Ala Glu Val Glu Lys
            20                  25                  30

Pro Gly Ala Ser Val Lys Val Ser Cys Lys Ala Ser Gly Tyr Thr Phe
        35                  40                  45

Thr Ser Tyr Trp Ile Thr Trp Val Arg Gln Ala Pro Gly Gln Gly Leu
    50                  55                  60

Glu Trp Met Gly Asp Ile Tyr Pro Gly Ser Gly Asn Thr Asn Tyr Asn
65                  70                  75                  80

Glu Lys Phe Lys Thr Arg Val Thr Ile Thr Ala Asp Lys Ser Thr Ser
                85                  90                  95
```

```
Thr Ala Tyr Met Glu Leu Ser Ser Leu Arg Ser Glu Asp Thr Ala Val
            100                 105                 110

Tyr Tyr Cys Ala Lys Glu Gly Gly Leu Thr Thr Glu Asp Tyr Ala Leu
        115                 120                 125

Asp Tyr Trp Gly Gln Gly Thr Leu Val Thr Val Ser Ser Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
450                 455                 460

Ser Leu Gly Lys
465

<210> SEQ ID NO 27
<211> LENGTH: 238
<212> TYPE: PRT
<213> ORGANISM: Artificial Sequence
<220> FEATURE:
<223> OTHER INFORMATION: Synthetic polypeptide
```

<400> SEQUENCE: 27

Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Lys Gln
            35                  40                  45

Val Ser Thr Ser Gly Tyr Ser Tyr Met His Trp Tyr Gln Gln Lys Pro
    50                  55                  60

Gly Gln Ala Pro Arg Leu Leu Ile Tyr Leu Ala Ser Asn Leu Glu Ser
65                  70                  75                  80

Gly Ile Pro Pro Arg Phe Ser Gly Ser Gly Tyr Gly Thr Asp Phe Thr
                85                  90                  95

Leu Thr Ile Asn Asn Ile Glu Ser Glu Asp Ala Ala Tyr Tyr Phe Cys
            100                 105                 110

Gln His Ser Arg Glu Leu Pro Phe Thr Phe Gly Gln Gly Thr Lys Val
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 28
<211> LENGTH: 654
<212> TYPE: DNA
<213> ORGANISM: Artificial Sequence
<220> FEATURE:
<223> OTHER INFORMATION: Synthetic polynucleotide

<400> SEQUENCE: 28
gaaattgtgt tgacacagtc tccagccacc ctgtctttgt ctccagggga aagagccacc    60
ctctcctgca gggccagcaa acaggtcagt acatctggct atagttatat gcactggtac   120
cagcagaaac ctggccaggc tcccaggctc ctcatctatc ttgcatccaa cctagaatct   180
gggatcccac ctcgattcag tggcagcggg tatggaacag attttaccct cacaattaat   240
aacatagaat ctgaggatgc tgcatattac ttctgtcagc acagtaggga gcttccattc   300
acgttcggcc aagggaccaa ggtggaaatc aaacgtacgg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480

```
ggtaactccc aggagagtgt cacagagcag gacagcaagg acagcaccta cagcctcagc        540
agcaccctga cgctgagcaa agcagactac gagaaacaca aagtctacgc ctgcgaagtc        600
acccatcagg gcctgagctc gcccgtcaca aagagcttca caggggaga gtgt              654
```

ANTI-CD73 ANTIBODIES

CROSS REFERENCE TO RELATED APPLICATIONS

This application is a continuation of U.S. patent application Ser. No. 15/647,212, filed Jul. 11, 2017, which issued as U.S. Pat. No. 10,793,636 on Oct. 6, 2020, which claims priority to U.S. Provisional Application No. 62/360,804, filed Jul. 11, 2016, and U.S. Provisional Application No. 62/395,875, filed Sep. 16, 2016, which are hereby incorporated by reference in their entirety and for all purposes.

REFERENCE TO A SEQUENCE LISTING, A TABLE OR A COMPUTER PROGRAM LISTING APPENDIX SUBMITTED AS AN ASCII TEXT FILE

The Sequence Listing written in file 048517-519C01US_SEQUENCE_LISTING_ST25.txt, created on Aug. 26, 2020, 36,327 bytes, machine format IBM-PC, MS Windows operating system, is hereby incorporated by reference.

BACKGROUND OF THE INVENTION

To ensure proper safety and efficacy profiles of novel and biosimilar mononclonal antibodies (mAb), it is necessary to understand the impact of glycosylation and to control glycosylation of product candidates. Depending on the expression host, glycosylation patterns in mAb or Fc-fusions can be significantly different, thus significantly impacting the pharmacokinetics (PK) and pharmacodynamics (PD) of mAbs. Glycans that may have an impact on PK and PD of mAb or Fc-fusion proteins include mannose, sialic acids, fucose, and galactose. Mannosylated glycans can impact the PK of the molecule, leading to reduced exposure and potentially lower efficacy. The level of sialic acid, N-acetylneuraminic acid (NANA), can also have a significant impact on the PK of Fc-fusion molecule. Glycans may also have impacts on the safety of mAbs. mAbs produced in murine myeloma cells such as NS0 and SP2/0 contain glycans such as Gal$\alpha$1-3Gal$\beta$1-4N-acetylglucosamine-R and N-glycolylneuraminic acid (NGNA) that are not naturally present in humans and can be immunogenic when used as therapeutics. The antibodies and methods of using the same provided herein address these and other needs in the art.

BRIEF SUMMARY OF THE INVENTION

In one aspect, a non-glycosylated antibody (e.g. an anti-CD73 antibody) is provided. The antibody includes (i) a CDR L1 of SEQ ID NO:1 and (ii) an amino acid substitution selected from the group consisting of: (a) any amino acid other than asparagine at a position corresponding to Kabat position 27A of SEQ ID NO:1; (b) any amino acid other than valine at a position corresponding to Kabat position 27B of SEQ ID NO:1; or (c) any amino acid other than serine at a position corresponding to Kabat position 27C of SEQ ID NO:1.

In one aspect, an anti-CD73 antibody is provided. The antibody includes (i) a CDR L1 of SEQ ID NO:1 and (ii) an amino acid substitution selected from the group consisting of: (a) any amino acid other than asparagine at a position corresponding to Kabat position 27A of SEQ ID NO:1; (b) any amino acid other than valine at a position corresponding to Kabat position 27B of SEQ ID NO:1; or (c) any amino acid other than serine at a position corresponding to Kabat position 27C of SEQ ID NO:1.

In one aspect, an isolated nucleic acid encoding a non-glycosylated antibody (e.g. an anti-CD73 antibody) provided herein including embodiments thereof is provided.

In one aspect, an isolated nucleic acid encoding an anti-CD73 antibody provided herein including embodiments thereof is provided.

In another aspect, a pharmaceutical composition including a therapeutically effective amount of a non-glycosylated antibody (e.g. an anti-CD73 antibody) provided herein including embodiments thereof and a pharmaceutically acceptable excipient is provided.

In another aspect, a pharmaceutical composition including a therapeutically effective amount of an anti-CD73 antibody provided herein including embodiments thereof and a pharmaceutically acceptable excipient is provided.

In one aspect, a method of treating cancer in a subject in need thereof is provided. The method includes administering to the subject a therapeutically effective amount of a non-glycosylated antibody (e.g. an anti-CD73 antibody) provided herein including embodiments thereof, thereby treating cancer in the subject.

In one aspect, a method of treating cancer in a subject in need thereof is provided. The method includes administering to the subject a therapeutically effective amount of an anti-CD73 antibody provided herein including embodiments thereof, thereby treating cancer in the subject.

In another aspect a non-glycosylated antibody (e.g., anti-CD73 antibody) is provided. The non-glycosylated antibody binds the same epitope as a 1E9 antibody, wherein the 1E9 antibody includes a humanized light chain variable region including a mouse CDR L1, mouse CDR L2, or mouse CDR L3 and a humanized heavy chain variable region including a mouse CDR H1, mouse CDR H2, or mouse CDR H3.

In another aspect a non-glycosylated antibody (e.g., anti-CD73 antibody) is provided. The non-glycosylated antibody binds the same epitope as a 1E9 antibody, wherein the 1E9 antibody includes a humanized light chain variable region and a humanized heavy chain variable region. The humanized light chain variable region includes:
(i) a mouse CDR L1 as set forth in SEQ ID NO:1, a mouse CDR L2 as set forth in SEQ ID NO:2, a mouse CDR L3 as set forth in SEQ ID NO:3 and
(ii) a valine at a position corresponding to Kabat position 2, a methionine at a position corresponding to Kabat position 4, an aspartic acid or a leucine at a position corresponding to Kabat position 9, a proline or a serine at a position corresponding to Kabat position 12, a lysine or a proline at a position corresponding to Kabat position 18, a alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a lysine at a position corresponding to Kabat position 78, a serine or an alanine at a position corresponding to Kabat position 80, a glutamine at a position corresponding to Kabat position 100, a valine at a position corresponding to Kabat position 104, a glutamic acid or an alanine at a position corresponding to Kabat position 1, a glutamine at a position corresponding to Kabat position 3, a phenylalanine or a threonine at a position corresponding to Kabat position 10, a glutamine at a position corresponding to Kabat position 11, an alanine or a leucine at a position corresponding to Kabat position 13, a threonine at a position corresponding to Kabat position 14, a valine or a proline at a position corresponding to Kabat position 15, a lysine at a position corresponding to Kabat position 16, a glutamic acid or an aspartic acid at a position corresponding to Kabat position 17, a threonine at a position corresponding to Kabat position 22, a lysine at a position corresponding to Kabat position 42, an arginine at a position corresponding to Kabat position 45, an isoleucine at a position corresponding to Kabat position 58, a tyrosine at a position corresponding to Kabat position 67, a phenylalanine at a position corresponding to Kabat position 73, an isoleucine at a position corresponding to Kabat position 78, a tyrosine at a position corresponding to Kabat position 85, or a phenylalanine at a position corresponding to Kabat position 87. The humanized heavy chain variable region includes:

(iii) a mouse CDR H1 as set forth in SEQ ID NO:4, a mouse CDR H2 as set forth in SEQ ID NO:5, and a mouse CDR H3 as set forth in SEQ ID NO:6 and (iv) an isoleucine at a position corresponding to Kabat position 37, an alanine or a proline at a position corresponding to Kabat position 40, a lysine at a position corresponding to Kabat position 43, a serine at a position corresponding to Kabat position 70, an isoleucine or a threonine at a position corresponding to Kabat position 75, a tryptophan at a position corresponding to Kabat position 82, an arginine or a lysine at a position corresponding to Kabat position 83, a alanine at a position corresponding to Kabat position 84, a serine at a position corresponding to Kabat position 85, a valine or a methionine at a position corresponding to Kabat position 89, a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, a threonine at a position corresponding to Kabat position 87, a glutamic acid at a position corresponding to Kabat position 1, a valine at a position corresponding to Kabat position 24, a arginine at a position corresponding to Kabat position 44, a methionine at a position corresponding to Kabat position 48, a leucine at a position corresponding to Kabat position 80, or a glutamic acid at a position corresponding to Kabat position 81.

BRIEF DESCRIPTION OF THE DRAWINGS

FIG. 7: Human PBMCs from 2 representative donors were labeled with CellTrace™ Violet, stimulated with anti-CD3 and anti-CD28 antibodies, and cultured in the presence of 3 mM AMP with either CPX006 (glycosylated antibody), CPX008 (aglycosylated antibody), or hIgG1 (isotype control) for 4 days. Proliferation of CD3+ cells was assessed by CellTrace™ Violet dilution using flow cytometry. CellTrace™ Violet Dim cells are CD3+ cells that have undergone two or more rounds of CellTrace™ Violet dilution and are plotted as a proportion of the total CD3+ population.

DETAILED DESCRIPTION OF THE INVENTION

Figure 1:
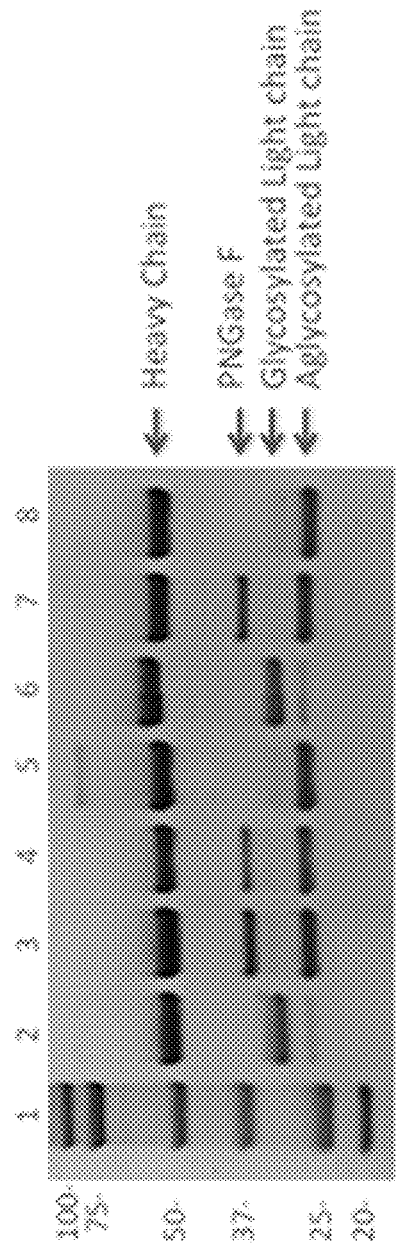
FIG. 1: PNGase F (Peptide-N-Glycosidase F) Treatment Eliminates N-linked Glycosylation on CDR L1 of CPX-006 and 1E9 (hybridoma). Lane 1: molecular weight marker (kaleidoscope); lane 2: CPX-006, glycosylated (mock treatment); lane 3: CPX-600 deglycosylated (2×PNGase F); lane 4: CPX-006 deglycosylated (1×PNGase F); lane 5: hIgG1 isotype control; lane 6: 1E9-mIgG3, glycosylated (mock treatment); lane 7: 1E9-mIgG3, deglycosylated (1×PNGase F); lane 8: mIgG3 isotype control.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

The terms "CDR L1", "CDR L2" and "CDR L3" as provided herein refer to the complementarity determining regions (CDR) 1, 2, and 3 of the variable light (L) chain of an antibody. In embodiments, the variable light chain provided herein includes in N-terminal to C-terminal direction a CDR L1, a CDR L2 and a CDR L3. Likewise, the terms "CDR H1", "CDR H2" and "CDR H3" as provided herein refer to the complementarity determining regions (CDR) 1, 2, and 3 of the variable heavy (H) chain of an antibody. In embodiments, the variable heavy chain provided herein includes in N-terminal to C-terminal direction a CDR H1, a CDR H2 and a CDR H3.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce F(ab)$'_2$, a dimer of Fab which itself is a light chain joined to $V_H$-$C_{H1}$ by a disulfide bond. The F(ab)$'_2$ may be reduced under mild conditions to break the disulfide linkage in the hinge region, thereby converting the F(ab)$'_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4:72 (1983); Cole et al., pp. 77-96 in *Monoclonal Antibodies and Cancer Therapy* (1985)). "Monoclonal" antibodies (mAb) refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348: 552-554 (1990); Marks et al., *Biotechnology* 10:779-783 (1992)).

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., *Cancer Res.* 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

A "ligand" refers to an agent, e.g., a polypeptide or other molecule, capable of binding to a receptor.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, an anti-CD73 antibody as described herein and a CD73 antigen. In embodiments contacting includes, for example, allowing an anti-CD73 antibody as described herein to interact with a CD73 antigen.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic (e.g., a non-naturally occurring amino acid) of a corresponding naturally occurring amino acid, as well as to naturally occurring amino acid polymers and non-naturally occurring amino acid polymers.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

A "conservative substitution" as used with respect to amino acids, refers to the substitution of an amino acid with a chemically similar amino acid. Amino acid substitutions which often preserve the structural and/or functional properties of the polypeptide in which the substitution is made are known in the art and are described, for example, by H. Neurath and R. L. Hill, 1979, in "The Proteins," Academic Press, New York. The most commonly occurring exchanges are isoleucine/valine, tyrosine/phenylalanine, aspartic acid/glutamic acid, lysine/arginine, methionine/leucine, aspartic acid/asparagine, glutamic acid/glutamine, leucine/isoleucine, methionine/isoleucine, threonine/serine, tryptophan/phenylalanine, tyrosine/histidine, tyrosine/tryptophan, glutamine/arginine, histidine/asparagine, histidine/glutamine, lysine/asparagine, lysine/glutamine, lysine/glutamic acid, phenylalanine/leucine, phenylalanine/methionine, serine/alanine, serine/asparagine, valine/leucine, and valine/methionine. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, there may be at least 1, at least 2, at least 3, at least 4, at least 5, at least 6, at least 7, at least 8, at least 9, at least 10, at least 15, at least 20, at least 25, at least 30, at least 35, or at least 40 conservative substitutions. In some embodiments, there may be 1, 2, 3, 4, 5, 6, 7, 8, 9, 10, 15, 20, 25, 30, 35, or 40 conservative substitutions.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

An amino acid or nucleotide base "position" is denoted by a number that sequentially identifies each amino acid (or nucleotide base) in the reference sequence based on its position relative to an N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to a reference sequence. In embodiments, the reference sequence is a CDR L1 having SEQ ID NO: 1. In embodiments, the comparison to the reference sequence is a sequence alignment between the given amino acid or polynucleotide sequence and the reference sequence.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci.* USA 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=-4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=-4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

An amino acid residue in an antibody "corresponds" to a given residue when it occupies the same essential structural position within the antibody as the given residue. For example, a selected residue in a comparison antibody corresponds to position 27A (according to the Kabat numbering system as described herein) in an antibody provided herein when the selected residue occupies the same essential spatial or structural relationship to Kabat position 27A as assessed using applicable methods in the art. For example, a comparison antibody may be aligned for maximum sequence homology with the antibody provided herein and the position in the aligned comparison antibody that aligns with Kabat position 27A may be determined to correspond to it. Alternatively, instead of (or in addition to) a primary sequence alignment as described above, a three dimensional structural alignment can also be used, e.g., where the structure of the comparison antibody is aligned for maximum correspondence with an antibody provided herein and the overall structures compared. In this case, an amino acid that occupies the same essential position as Kabat position 27A in the structural model may be said to correspond.

The term "isolated," when applied to a protein, denotes that the protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. The term "purified" denotes that a protein gives rise to essentially one band in an electrophoretic gel. Particularly, it means that the protein is at least 85% pure, more preferably at least 95% pure, and most preferably at least 99% pure.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Typically a specific or selective reaction will be at least twice background signal or noise and more typically more than 10 to 100 times background.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells.

As defined herein, the term "inhibition", "inhibit", "inhibiting" and the like in reference to a protein-inhibitor (e.g., an anti-CD73 antibody) interaction means negatively affecting (e.g., decreasing) the activity or function of the protein (e.g., decreasing the catalytic activity of CD73) relative to the activity or function of the protein in the absence of the inhibitor (e.g., an anti-CD73 antibody). In some embodiments inhibition refers to reduction of a disease or symptoms of disease. Thus, inhibition includes, at least in part, partially or totally blocking stimulation, decreasing, preventing, or delaying activation, or inactivating, desensitizing, or down-regulating signal transduction or enzymatic activity or the amount of a protein. Similarly an "inhibitor" is a compound or protein that inhibits CD73 activity, e.g., by binding, partially or totally blocking, decreasing, preventing, delaying, inactivating, desensitizing, or down-regulating enzymatic activity (e.g., CD73 catalytic activity).

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pennsylvania, 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

The compositions can be administered for therapeutic or prophylactic treatments. In therapeutic applications, compositions are administered to a patient suffering from a disease (e.g., cancer) in a "therapeutically effective dose" or "therapeutically effective amount." Amounts effective for this use will depend upon the severity of the disease and the general state of the patient's health. Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

The compositions provided herein, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

The combined administrations contemplates co-administration, using separate formulations or a single pharmaceutical formulation, and consecutive administration in either order, wherein preferably there is a time period while both (or all) active agents simultaneously exert their biological activities.

Effective doses of the compositions provided herein vary depending upon many different factors, including means of administration, target site, physiological state of the patient, whether the patient is human or an animal, other medications administered, and whether treatment is prophylactic or therapeutic. However, a person of ordinary skill in the art would immediately recognize appropriate and/or equivalent doses looking at dosages of approved compositions for treating and preventing cancer for guidance.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). The disease may be an autoimmune, inflammatory, cancer, infectious, metabolic, developmental, cardiovascular, liver, intestinal, endocrine, neurological, or other disease.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, Herceptin™ resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

Humanized Antibodies

A humanized antibody is a genetically engineered antibody in which at least one CDR (or functional fragment thereof) from a mouse antibody ("donor antibody", which can also be rat, hamster or other non-human species) is grafted onto a human antibody ("acceptor antibody"). The human antibody is a non-natural (e.g. not naturally occurring or not naturally produced by a human) antibody that does not elicit an immune response in a human, does not elicit a significant immune response in a human, or elicits an immune response that is less than the immune response elicited in a mouse. In embodiments, more than one mouse CDR is grafted (e.g. all six mouse CDRs are grafted). The sequence of the acceptor antibody can be, for example, a mature human antibody sequence (or fragment thereof), a consensus sequence of a human antibody sequence (or fragment thereof), or a germline region sequence (or fragment thereof). Thus, a humanized antibody may be an antibody having one or more CDRs from a donor antibody and a variable region framework (FR). The FR may form part of a constant region and/or a variable region within a human antibody. In addition, in order to retain high binding affinity, amino acids in the human acceptor sequence may be replaced by the corresponding amino acids from the donor sequence, for example where: (1) the amino acid is in a CDR; (2) the amino acid is in the human framework region (e.g. the amino acid is immediately adjacent to one of the CDR's). See, U.S. Pat. Nos. 5,530,101 and 5,585,089, incorporated herein by reference, which provide detailed instructions for construction of humanized antibodies. Although humanized antibodies often incorporate all six CDRs (e.g. as defined by Kabat, but often also including hypervariable loop H1 as defined by Chothia) from a mouse antibody, they can also be made with fewer mouse CDRs and/or less than the complete mouse CDR sequence (e.g. a functional fragment of a CDR) (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

Typically a humanized antibody as provided herein may include (i) a light chain comprising at least one CDR (e.g., a CDR L1 of SEQ ID NO:1; often three CDRs) from a mouse antibody (also referred to herein as a mouse CDR) and a human variable region framework; and (ii) a heavy chain comprising at least one CDR (e.g., a CR H1 of SEQ ID NO:4; often three CDRs) from the mouse antibody and a human variable region framework (FR). The light and heavy chain variable region frameworks (FRs) may each be a mature human antibody variable region framework sequence (or fragment thereof), a germline variable region framework sequence (combined with a J region sequence) (or fragment thereof), or a consensus sequence of a human antibody variable region framework sequence (or fragment thereof). In embodiments, the humanized antibody includes a light chain as described in (i), a heavy chain as described in (ii) together with a light chain human constant region and a heavy chain constant region.

A chimeric antibody is an antibody in which the variable region of a mouse (or other rodent) antibody is combined with the constant region of a human antibody; their construction by means of genetic engineering is well-known. Such antibodies retain the binding specificity of the mouse antibody, while being about two-thirds human. The proportion of nonhuman sequence present in mouse, chimeric and humanized antibodies suggests that the immunogenicity of chimeric antibodies is intermediate between mouse and humanized antibodies. Other types of genetically engineered antibodies that may have reduced immunogenicity relative to mouse antibodies include human antibodies made using phage display methods (Dower et al., WO91/17271; McCafferty et al., WO92/001047; Winter, WO92/20791; and Winter, FEBS Lett. 23:92, 1998, each of which is incorporated herein by reference) or using transgenic animals (Lonberg et al., WO93/12227; Kucherlapati WO91/10741, each of which is incorporated herein by reference).

Other approaches to design humanized antibodies may also be used to achieve the same result as the methods in U.S. Pat. Nos. 5,530,101 and 5,585,089 described above, for example, "superhumanization" (see Tan et al. J. Immunol. 169: 1119, 2002, and U.S. Pat. No. 6,881,557) or the method of Studnicak et al., Protein Eng. 7:805, 1994. Moreover, other approaches to produce genetically engineered, reduced-immunogenicity mAbs include "reshaping", "hyperchimerization" and veneering/resurfacing, as described, e.g., in Vaswami et al., Annals of Allergy, Asthma and Immunology 81:105, 1998; Roguska et al. Protein Eng. 9:895, 1996; and U.S. Pat. Nos. 6,072,035 and 5,639,641.

A "CD73 protein" or "CD73 antigen" as referred to herein includes any of the recombinant or naturally-occurring forms of the Cluster of Differentiation 73 (CD73) also known as 5'-nucleotidase (5'-NT) or ecto-5'-nucleotidase or variants or homologs thereof that maintain CD73 nucleotidase activity (e.g. within at least 50%, 80%, 90%, 95%, 96%, 97%, 98%, 99% or 100% activity compared to CD73). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD73 protein. In embodiments, the CD73 protein is substantially identical to the protein identified by the UniProt reference number P21589 or a variant or homolog having substantial identity thereto. In embodiments, the CD73 protein is substantially identical to the protein identified by the UniProt reference number Q61503 or a variant or homolog having substantial identity thereto.

Anti-CD73 Antibodies

Provided herein are, inter alia, antibodies capable of binding CD73 and inhibiting CD73 activity. The antibodies provided herein include amino acid substitutions, which, inter alia, prevent the antibody from being glycosylated. A "glycosylated" antibody as referred to herein is an antibody or functional fragment thereof which includes a glycan moiety bound to one or more of the antibody's or antibody fragment's amino acids. The glycan moiety may be bound to a nitrogen atom of the amino acid (e.g., the amide nitrogen of an asparagine) of the antibody or functional fragment thereof. In embodiments, the glycan moiety is attached to the amino acid through post-translational modification. In embodiments, the glycan moiety is a mannose moiety, a sialic acid moiety, a fucose moiety or a galactose moiety. Therefore, a "non-glycosylated" or "aglycosylated" antibody or functional fragment thereof (e.g., an aglycosylated light chain) refers to an antibody or functional fragment thereof, where a glycan moiety is not attached to an amino acid residue at a position corresponding to a glycosylated amino acid residue in a control antibody (e.g., an anti-CD73 antibody including a glycosylated amino acid at that corresponding position). The anti-CD73 antibodies provided herein may be aglycosylated. In embodiments, the anti-CD73 antibody provided herein includes one or more aglycosylated amino acid residues. Thus, in embodiments, the anti-CD73 antibody is non-glycosylated. In embodiments, the anti-CD73 antibody provided herein includes one or more non-glycosylated amino acid residues. In embodiments, the anti-CD73 antibody includes a non-glycosylated amino acid at a position corresponding to Kabat position 27A. The antibody (e.g. anti-CD73 antibody) provided herein may include an amino acid substitution at a position corresponding to Kabat position 27A, 27B, or 27C of SEQ ID NO:1 and said amino acid substitution may prevent the amino acid at a position corresponding to Kabat position 27A of being glycosylated. The aglycosylated anti-CD73 antibodies provided herein are capable of binding CD73 and inhibiting CD73 activity.

The anti-CD73 antibodies provided herein including embodiments thereof may include one or more amino acid substitutions at a position corresponding to a specific Kabat position (e.g., 27A, 27B, 27C of SEQ ID NO:1). In embodiments, the anti-CD73 antibody includes an amino acid substitution at a position corresponding to Kabat position 27A, 27B or 27C of SEQ ID NO:1. In embodiments, the anti-CD73 antibody includes an amino acid substitution at a position corresponding to Kabat position 27A of SEQ ID NO:1. In embodiments, the anti-CD73 antibody includes an amino acid substitution at a position corresponding to Kabat position 27B of SEQ ID NO:1. In embodiments, the anti-CD73 antibody includes an amino acid substitution at a position corresponding to Kabat position 27C of SEQ ID NO:1. In embodiments, the anti-CD73 antibody includes an amino acid substitution at a position corresponding to Kabat position 27A, 27B and 27C of SEQ ID NO:1.

An amino acid substitution as provided herein is an amino acid inserted in the place of an amino acid that has been previously removed. The residue (amino acid substitution) inserted may be any naturally or non-naturally occurring amino acid. The amino acid substitution may be any of the twenty amino acids commonly found in proteins except for: asparagine, wherein the substitution is at a position corresponding to Kabat position 27A; valine, wherein the substitution is at a position corresponding to Kabat position 27B; or serine, wherein the substitution is at a position corresponding to Kabat position 27C. The amino acid substitution may be a substitution of one amino acid residue for another within the same class or group and is referred to herein as a "conservative" substitution. Conservative amino acid substitutions can frequently be made in a protein without significantly altering the conformation or function of the protein (e.g., anti-CD73 antibody). Substitution of one amino acid residue for another from a different class or group is referred to herein as a "non-conservative" substitution. In embodiments, non-conservative amino acid substitutions modify conformation and/or function of a protein.
Examples of Amino Acid Classification
Small/Aliphatic residues: Gly, Ala, Val, Leu, Ile
Cyclic Imino Acid: Pro
Hydroxyl-containing Residues: Ser, Thr
Acidic Residues: Asp, Glu
Amide Residues: Asn, Gln
Basic Residues: Lys, Arg
Imidazole Residue: His
Aromatic Residues: Phe, Tyr, Trp
Sulfur-containing Residues: Met, Cys In embodiments, the conservative amino acid substitution comprises substituting any of glycine (G), alanine (A), isoleucine (I), valine (V), and leucine (L) for any other of these aliphatic amino acids; serine (S) for threonine (T) and vice versa; aspartic acid (D) for glutamic acid (E) and vice versa; glutamine (Q) for asparagine (N) and vice versa; lysine (K) for arginine (R) and vice versa; phenylalanine (F), tyrosine (Y) and tryptophan (W) for any other of these aromatic amino acids; and methionine (M) for cysteine (C) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g., BIOCHEMISTRY at pp. 13-15, 2nd ed. Lubert Stryer ed. (Stanford University); Henikoff et al., *Proc. Nat'l Acad. Sci. USA* (1992) 89:10915-10919; Lei et al., *J. Biol. Chem.* (1995) 270(20):11882-11886).

In one aspect, an anti-CD73 antibody is provided. The antibody includes (i) a CDR L1 of SEQ ID NO:1 and (ii) an amino acid substitution selected from the group consisting of: (a) any amino acid other than asparagine at a position corresponding to Kabat position 27A of SEQ ID NO:1; (b) any amino acid other than valine at a position corresponding to Kabat position 27B of SEQ ID NO:1; or (c) any amino acid other than serine at a position corresponding to Kabat position 27C of SEQ ID NO:1. In embodiments, the amino acid substitution is an unnatural amino acid. In embodiments, the anti-CD73 antibody includes an amino acid substitution at a position corresponding to Kabat position 27A and the amino acid at a position corresponding to Kabat position 27B and/or Kabat position 27C remains unsubstituted. In embodiments, the anti-CD73 antibody includes an amino acid substitution at a position corresponding to Kabat position 27B and the amino acid at a position corresponding to Kabat position 27A and/or Kabat position 27C remains unsubstituted. In embodiments, the anti-CD73 antibody includes an amino acid substitution at a position corresponding to Kabat position 27C and the amino acid at a position corresponding to Kabat position 27A and/or Kabat position 27B remains unsubstituted.

In embodiments, the amino acid other than asparagine is a glycine, an alanine, a leucine, a methionine, a phenylalanine, a tryptophan, a lysine, a glutamine, a glutamic acid, a serine, a proline, a valine, an isoleucine, a cysteine, a tyrosine, a histidine, an arginine, an aspartic acid or a threonine at a position corresponding to Kabat position 27A. In embodiments, the amino acid other than asparagine is an alanine, a glycine, a glutamine, an aspartic acid or an arginine at a position corresponding to Kabat position 27A. In embodiments, the amino acid other than asparagine is a glycine at a position corresponding to Kabat position 27A. In embodiments, the amino acid other than asparagine is an alanine at a position corresponding to Kabat position 27A. In embodiments, the amino acid other than asparagine is a leucine at a position corresponding to Kabat position 27A. In embodiments, the amino acid other than asparagine is a methionine at a position corresponding to Kabat position 27A. In embodiments, the amino acid other than asparagine is a phenylalanine at a position corresponding to Kabat position 27A. In embodiments, the amino acid other than asparagine is a tryptophan at a position corresponding to Kabat position 27A. In embodiments, the amino acid other than asparagine is a lysine at a position corresponding to Kabat position 27A. In embodiments, the amino acid other than asparagine is a glutamine at a position corresponding to Kabat position 27A. In embodiments, the amino acid other than asparagine is a glutamic acid at a position corresponding to Kabat position 27A.

In embodiments, the amino acid other than asparagine is a serine at a position corresponding to Kabat position 27A. In embodiments, the amino acid other than asparagine is a proline at a position corresponding to Kabat position 27A. In embodiments, the amino acid other than asparagine is a valine at a position corresponding to Kabat position 27A. In embodiments, the amino acid other than asparagine is an isoleucine at a position corresponding to Kabat position 27A. In embodiments, the amino acid other than asparagine is a cysteine at a position corresponding to Kabat position 27A. In embodiments, the amino acid other than asparagine is a tyrosine at a position corresponding to Kabat position 27A. In embodiments, the amino acid other than asparagine is a histidine at a position corresponding to Kabat position 27A. In embodiments, the amino acid other than asparagine is an arginine at a position corresponding to Kabat position 27A. In embodiments, the amino acid other than asparagine is an aspartic acid at a position corresponding to Kabat position 27A. In embodiments, the amino acid other than asparagine is a threonine at a position corresponding to Kabat position 27A. In one further embodiment, the anti-CD73 antibody includes a glycine, an alanine, a leucine, a methionine, a phenylalanine, a tryptophan, a lysine, a glutamine, a glutamic acid, a serine, a proline, a valine, an isoleucine, a cysteine, a tyrosine, a histidine, an arginine, an asparagine, an aspartic acid or a threonine at a position corresponding to Kabat position 27B. In another further embodiment, the anti-CD73 antibody includes a glycine, an alanine, a leucine, a methionine, a phenylalanine, a tryptophan, a lysine, a glutamine, a glutamic acid, a serine, a proline, a valine, an isoleucine, a cysteine, a tyrosine, a histidine, an arginine, an asparagine, an aspartic acid or a threonine at a position corresponding to Kabat position 27C.

In embodiments, the amino acid other than valine is a glycine, an alanine, a leucine, a methionine, a phenylalanine, a tryptophan, a lysine, a glutamine, a glutamic acid, a serine, a proline, an isoleucine, a cysteine, a tyrosine, a histidine, an arginine, an asparagine, an aspartic acid or a threonine at a position corresponding to Kabat position 27B. In embodiments, the amino acid other than valine is a glycine at a position corresponding to Kabat position 27B. In embodiments, the amino acid other than valine is an alanine at a position corresponding to Kabat position 27B. In embodiments, the amino acid other than valine is a leucine at a position corresponding to Kabat position 27B. In embodiments, the amino acid other than valine is methionine at a position corresponding to Kabat position 27B. In embodiments, the amino acid other than valine is a phenylalanine at a position corresponding to Kabat position 27B. In embodiments, the amino acid other than valine is a tryptophan at a position corresponding to Kabat position 27B. In embodiments, the amino acid other than valine is a lysine at a position corresponding to Kabat position 27B. In embodiments, the amino acid other than valine is a glutamine at a position corresponding to Kabat position 27B. In embodiments, the amino acid other than valine is a glutamic acid at a position corresponding to Kabat position 27B. In embodiments, the amino acid other than valine is a serine at a position corresponding to Kabat position 27B. In embodiments, the amino acid other than valine is a proline at a position corresponding to Kabat position 27B. In embodiments, the amino acid other than valine is an isoleucine at a position corresponding to Kabat position 27B. In embodiments, the amino acid other than valine is a cysteine at a position corresponding to Kabat position 27B. In embodiments, the amino acid other than valine is a tyrosine at a position corresponding to Kabat position 27B. In embodiments, the amino acid other than valine is a histidine at a position corresponding to Kabat position 27B. In embodiments, the amino acid other than valine is an arginine at a position corresponding to Kabat position 27B. In embodiments, the amino acid other than valine is an asparagine at a position corresponding to Kabat position 27B. In embodiments, the amino acid other than valine is an aspartic acid at a position corresponding to Kabat position 27B. In embodiments, the amino acid other than valine is a threonine at a position corresponding to Kabat position 27B. In one further embodiment, the anti-CD73 antibody includes a glycine, an alanine, a leucine, a methionine, a phenylalanine, a tryptophan, a lysine, a glutamine, a glutamic acid, a serine, a proline, a valine, an isoleucine, a cysteine, a tyrosine, a histidine, an arginine, an asparagine, an aspartic acid or a threonine at a position corresponding to Kabat position 27C. In another further embodiment, the anti-CD73 antibody includes a glycine, an alanine, a leucine, a methionine, a phenylalanine, a tryptophan, a lysine, a glutamine, a glutamic acid, a serine, a proline, a valine, an isoleucine, a cysteine, a tyrosine, a histidine, an arginine, an asparagine, an aspartic acid or a threonine at a position corresponding to Kabat position 27A.

In embodiments, the amino acid other than serine is a glycine, an alanine, a leucine, a methionine, a phenylalanine, a tryptophan, a lysine, a glutamine, a glutamic acid, a proline, a valine, an isoleucine, a cysteine, a tyrosine, a histidine, an arginine, an asparagine, an aspartic acid or a threonine at a position corresponding to Kabat position 27C. In embodiments, the amino acid other than serine is a glycine at a position corresponding to Kabat position 27C. In embodiments, the amino acid other than serine is an alanine at a position corresponding to Kabat position 27C. In embodiments, the amino acid other than serine is a leucine at a position corresponding to Kabat position 27C. In embodiments, the amino acid other than serine is a methionine at a position corresponding to Kabat position 27C. In embodiments, the amino acid other than serine is a phenylalanine at a position corresponding to Kabat position 27C. In embodiments, the amino acid other than serine is a tryptophan at a position corresponding to Kabat position 27C. In embodiments, the amino acid other than serine is a lysine at a position corresponding to Kabat position 27C. In embodiments, the amino acid other than serine is a glutamine at a position corresponding to Kabat position 27C. In embodiments, the amino acid other than serine is a glutamic acid at a position corresponding to Kabat position 27C. In embodiments, the amino acid other than serine is a proline at a position corresponding to Kabat position 27C. In embodiments, the amino acid other than serine is a valine at a position corresponding to Kabat position 27C. In embodiments, the amino acid other than serine is an isoleucine at a position corresponding to Kabat position 27C. In embodiments, the amino acid other than serine is a cysteine at a position corresponding to Kabat position 27C. In embodiments, the amino acid other than serine is a tyrosine at a position corresponding to Kabat position 27C. In embodiments, the amino acid other than serine is a histidine at a position corresponding to Kabat position 27C. In embodiments, the amino acid other than serine is an arginine at a position corresponding to Kabat position 27C. In embodiments, the amino acid other than serine is an asparagine at a position corresponding to Kabat position 27C. In embodiments, the amino acid other than serine is an aspartic acid at a position corresponding to Kabat position 27C. In embodiments, the amino acid other than serine is a threonine at a position corresponding to Kabat position 27C. In one further embodiment, the anti-CD73 antibody includes a glycine, an alanine, a leucine, a methionine, a phenylalanine, a tryptophan, a lysine, a glutamine, a glutamic acid, a serine, a proline, a valine, an isoleucine, a cysteine, a tyrosine, a histidine, an arginine, an asparagine, an aspartic acid or a threonine at a position corresponding to Kabat position 27A. In another further embodiment, the anti-CD73 antibody includes a glycine, an alanine, a leucine, a methionine, a phenylalanine, a tryptophan, a lysine, a glutamine, a glutamic acid, a serine, a proline, a valine, an isoleucine, a cysteine, a tyrosine, a histidine, an arginine, an asparagine, an aspartic acid or a threonine at a position corresponding to Kabat position 27B.

In embodiments, the amino acid other than valine is a proline at a position corresponding to Kabat position 27B. In one further embodiment, the anti-CD73 antibody includes an asparagine at a position corresponding to Kabat position 27A. In another further embodiment, the anti-CD73 antibody includes a serine at a position corresponding to Kabat position 27C. In a further embodiment, the anti-CD73 antibody includes a CDR L2 as set forth in SEQ ID NO:2, a CDR L3 as set forth in SEQ ID NO:3, a CDR H1 as set forth in SEQ ID NO:4, a CDR H2 as set forth in SEQ ID NO:5 and a CDR H3 as set forth in SEQ ID NO:6. In another further embodiment, the antibody includes a light chain variable region including the sequence of SEQ ID NO:7 or SEQ ID NO:8. In one embodiment, the anti-CD73 antibody includes a proline at a position corresponding to Kabat position 27B, an asparagine at a position corresponding to Kabat position 27A, a serine at a position corresponding to Kabat position 27C. In one embodiment, the anti-CD73 antibody includes a proline at a position corresponding to Kabat position 27B, an asparagine at a position corresponding to Kabat position 27A, a serine at a position corresponding to Kabat position 27C, a CDR L2 as set forth in SEQ ID NO:2, a CDR L3 as set forth in SEQ ID NO:3, a CDR H1 as set forth in SEQ ID NO:4, a CDR H2 as set forth in SEQ ID NO:5 and a CDR H3 as set forth in SEQ ID NO: 6.

In embodiments, the amino acid other than asparagine is a glutamine at a position corresponding to Kabat position 27A. In one further embodiment, the anti-CD73 antibody includes a valine at a position corresponding to Kabat position 27B. In another further embodiment, the anti-CD73 antibody includes a serine at a position corresponding to Kabat position 27C. In a further embodiment, the anti-CD73 antibody includes a CDR L2 as set forth in SEQ ID NO:2, a CDR L3 as set forth in SEQ ID NO:3, a CDR H1 as set forth in SEQ ID NO:4, a CDR H2 as set forth in SEQ ID NO:5 and a CDR H3 as set forth in SEQ ID NO:6. In another further embodiment, the antibody includes a light chain variable region including the sequence of SEQ ID NO:8. In another further embodiment, the antibody includes a light chain variable region including the sequence of SEQ ID NO:7. In another further embodiment, the antibody includes a light chain variable region including the sequence of SEQ ID NO:19. In another further embodiment, the antibody includes a light chain variable region including the sequence of SEQ ID NO:22. In one embodiment, the anti-CD73 antibody includes a glutamine at a position corresponding to Kabat position 27A, a valine at a position corresponding to Kabat position 27B, a serine at a position corresponding to Kabat position 27C. In one embodiment, the anti-CD73 antibody includes a glutamine at a position corresponding to Kabat position 27A, a valine at a position corresponding to Kabat position 27B, a serine at a position corresponding to Kabat position 27C, a CDR L2 as set forth in SEQ ID NO:2, a CDR L3 as set forth in SEQ ID NO:3, a CDR H1 as set forth in SEQ ID NO:4, a CDR H2 as set forth in SEQ ID NO:5 and a CDR H3 as set forth in SEQ ID NO:6.

In embodiments, the amino acid other than asparagine is an alanine at a position corresponding to Kabat position 27A. In one further embodiment, the anti-CD73 antibody includes a valine at a position corresponding to Kabat position 27B. In another further embodiment, the anti-CD73 antibody includes a serine at a position corresponding to Kabat position 27C. In a further embodiment, the anti-CD73 antibody includes a CDR L2 as set forth in SEQ ID NO:2, a CDR L3 as set forth in SEQ ID NO:3, a CDR H1 as set forth in SEQ ID NO:4, a CDR H2 as set forth in SEQ ID NO:5 and a CDR H3 as set forth in SEQ ID NO:6. In another further embodiment, the antibody includes a light chain variable region including the sequence of SEQ ID NO:8. In another further embodiment, the antibody includes a light chain variable region including the sequence of SEQ ID NO:20. In one embodiment, the anti-CD73 antibody includes an alanine at a position corresponding to Kabat position 27A, a valine at a position corresponding to Kabat position 27B and a serine at a position corresponding to Kabat position 27C. In one embodiment, the anti-CD73 antibody includes an alanine at a position corresponding to Kabat position 27A, a valine at a position corresponding to Kabat position 27B, a serine at a position corresponding to Kabat position 27C, a CDR L2 as set forth in SEQ ID NO:2, a CDR L3 as set forth in SEQ ID NO:3, a CDR H1 as set forth in SEQ ID NO:4, a CDR H2 as set forth in SEQ ID NO:5 and a CDR H3 as set forth in SEQ ID NO: 6.

In embodiments, the anti-CD73 antibody includes an asparagine at a position corresponding to Kabat position 27A and an alanine at a position corresponding to Kabat position 27C. In one further embodiment, the anti-CD73 antibody includes a valine at a position corresponding to Kabat position 27B. In a further embodiment, the anti-CD73 antibody includes a CDR L2 as set forth in SEQ ID NO:2, a CDR L3 as set forth in SEQ ID NO:3, a CDR H1 as set forth in SEQ ID NO:4, a CDR H2 as set forth in SEQ ID NO:5 and a CDR H3 as set forth in SEQ ID NO:6. In another further embodiment, the antibody includes a light chain variable region including the sequence of SEQ ID NO:8. In another further embodiment, the antibody includes a light chain variable region including the sequence of SEQ ID NO:21. In one embodiment, the anti-CD73 antibody includes an asparagine at a position corresponding to Kabat position 27A, an alanine at a position corresponding to Kabat position 27C and a valine at a position corresponding to Kabat position 27B. In one embodiment, the anti-CD73 antibody includes an asparagine at a position corresponding to Kabat position 27A, an alanine at a position corresponding to Kabat position 27C, a valine at a position corresponding to Kabat position 27B, a CDR L2 as set forth in SEQ ID NO:2, a CDR L3 as set forth in SEQ ID NO:3, a CDR H1 as set forth in SEQ ID NO:4, a CDR H2 as set forth in SEQ ID NO:5 and a CDR H3 as set forth in SEQ ID NO:6.

In embodiments, the amino acid other than asparagine is an aspartic acid at a position corresponding to Kabat position 27A. In one further embodiment, the anti-CD73 antibody includes a valine at a position corresponding to Kabat position 27B. In another further embodiment, the anti-CD73 antibody includes a serine at a position corresponding to Kabat position 27C. In a further embodiment, the anti-CD73 antibody includes a CDR L2 as set forth in SEQ ID NO:2, a CDR L3 as set forth in SEQ ID NO:3, a CDR H1 as set forth in SEQ ID NO:4, a CDR H2 as set forth in SEQ ID NO:5 and a CDR H3 as set forth in SEQ ID NO:6. In another further embodiment, the antibody includes a light chain variable region including the sequence of SEQ ID NO:8. In another further embodiment, the antibody includes a light chain variable region including the sequence of SEQ ID NO:23. In one embodiment, the anti-CD73 antibody includes an aspartic acid at a position corresponding to Kabat position 27A, a valine at a position corresponding to Kabat position 27B and a serine at a position corresponding to Kabat position 27C. In one embodiment, the anti-CD73 antibody includes an aspartic acid at a position corresponding to Kabat position 27A, a valine at a position corresponding to Kabat position 27B, a serine at a position corresponding to Kabat position 27C, a CDR L2 as set forth in SEQ ID NO:2, a CDR L3 as set forth in SEQ ID NO:3, a CDR H1 as set forth in SEQ ID NO:4, a CDR H2 as set forth in SEQ ID NO:5 and a CDR H3 as set forth in SEQ ID NO: 6.

In embodiments, the anti-CD73 antibody includes a CDR L2 as set forth in SEQ ID NO:2. In embodiments, the anti-CD73 antibody includes a CDR L3 as set forth in SEQ ID NO:3. In embodiments, the anti-CD73 antibody includes a CDR H1 as set forth in SEQ ID NO:4. In embodiments, the anti-CD73 antibody includes a CDR H2 as set forth in SEQ ID NO:5. In embodiments, the anti-CD73 antibody includes a CDR H3 as set forth in SEQ ID NO:6. In embodiments, the anti-CD73 antibody includes a CDR L1 as set forth in SEQ ID NO: 1, a CDR L2 as set forth in SEQ ID NO:2, a CDR L3 as set forth in SEQ ID NO:3, a CDR H1 as set forth in SEQ ID NO:4, a CDR H2 as set forth in SEQ ID NO:5 and a CDR H3 as set forth in SEQ ID NO:6.

In embodiments, the antibody includes a sequence of SEQ ID NO:26. In embodiments, the antibody includes a sequence of SEQ ID NO:27. In embodiments, the antibody includes a heavy chain and said heavy chain includes a sequence of SEQ ID NO:26. In further embodiments, the heavy chain is SEQ ID NO:26. In embodiments, the antibody includes a light chain and said light chain includes a sequence of SEQ ID NO:27. In further embodiments, the light chain is SEQ ID NO:27.

In embodiments, the antibody is a chimeric antibody. In embodiments, the antibody is a humanized antibody. In embodiments, the anti-CD73 antibody includes a light chain variable region of SEQ ID NO:7 or SEQ ID NO:8. In embodiments, the anti-CD73 antibody includes a light chain variable region of SEQ ID NO:7. In embodiments, the anti-CD73 antibody includes a light chain variable region of SEQ ID NO:8. In embodiments, the anti-CD73 antibody includes a heavy chain variable region of SEQ ID NO:9. In embodiments, the anti-CD73 antibody includes a light chain variable region of SEQ ID NO: 19. In embodiments, the anti-CD73 antibody includes a light chain variable region of SEQ ID NO:20. In embodiments, the anti-CD73 antibody includes a light chain variable region of SEQ ID NO:21. In embodiments, the anti-CD73 antibody includes a light chain variable region of SEQ ID NO:22. In embodiments, the anti-CD73 antibody includes a light chain variable region of SEQ ID NO:23.

In embodiments, the antibody is an IgG. The anti-CD73 antibody provided herein may be an IgG1, IgG2, IgG3 or IgG4. In embodiments, the antibody is an IgG1. In embodiments, the antibody is an IgG4. In embodiments, the antibody is an IgM. In embodiments, the antibody is an IgA. The anti-CD73 antibodies provided herein may be a Fab' fragment. Where the anti-CD73 antibody are Fab' fragments, the antibodies include a heavy chain (e.g. including a constant and a variable region) and a light chain (e.g. including a constant and a variable region). In embodiments, the anti-CD73 antibody is a Fab' fragment.

In embodiments, the antibody is a single chain antibody (scFv). A single chain antibody includes a variable light chain and a variable heavy chain. A person of skill in the art will immediately recognize that a single chain antibody includes a single light chain and a single heavy chain, in contrast to an immunoglobulin antibody, which includes two identical pairs of polypeptide chains, each pair having one light chain and one heavy chain. Each light chain and heavy chain in turn consists of two regions: a variable ("V") region (i.e. variable light chain and variable heavy chain) involved in binding the target antigen, and a constant ("C") region that interacts with other components of the immune system. The variable light chain and the variable heavy chain in a single chain antibody may be linked through a linker peptide. Examples for linker peptides of single chain antibodies are described in Bird, R. E., Hardman, K. D., Jacobson, J. W., Johnson, S., Kaufman, B. M., Lee, S. M., Lee, T., Pope, S. H., Riordan, G. S. and Whitlow, M. (1988). Methods of making scFv antibodies have been described. See, Huse et al., *Science* 246:1275-1281 (1989); Ward et al., *Nature* 341:544-546 (1989); and Vaughan et al., *Nature Biotech.* 14:309-314 (1996). Briefly, mRNA from B-cells from an immunized animal is isolated and cDNA is prepared. The cDNA is amplified using primers specific for the variable regions of heavy and light chains of immunoglobulins. The PCR products are purified and the nucleic acid sequences are joined. If a linker peptide is desired, nucleic acid sequences that encode the peptide are inserted between the heavy and light chain nucleic acid sequences. The nucleic acid which encodes the scFv is inserted into a vector and expressed in the appropriate host cell.

The ability of an antibody to bind a specific epitope (e.g., CD73) can be described by the equilibrium dissociation constant ($K_D$). The equilibrium dissociation constant ($K_D$) as defined herein is the ratio of the dissociation rate (K-off) and the association rate (K-on) of an antibody to a CD73 protein. It is described by the following formula: $K_D$=K-off/K-on. In embodiments, the antibody is capable of binding a CD73 antigen with an equilibrium dissociation constant ($K_D$) from about 0.5 to about 25 nM. In embodiments, the antibody is capable of binding a CD73 antigen with an equilibrium dissociation constant ($K_D$) from about 1 to about 25 nM. In embodiments, the antibody is capable of binding a CD73 antigen with an equilibrium dissociation constant ($K_D$) from about 1.5 to about 25 nM. In embodiments, the antibody is capable of binding a CD73 antigen with an equilibrium dissociation constant ($K_D$) from about 2 to about 25 nM. In embodiments, the antibody is capable of binding a CD73 antigen with an equilibrium dissociation constant ($K_D$) from about 2.5 to about 25 nM. In embodiments, the antibody is capable of binding a CD73 antigen with an equilibrium dissociation constant ($K_D$) from about 3 to about 25 nM. In embodiments, the antibody is capable of binding a CD73 antigen with an equilibrium dissociation constant ($K_D$) from about 3.5 to about 25 nM. In embodiments, the antibody is capable of binding a CD73 antigen with an equilibrium dissociation constant ($K_D$) from about 4 to about 25 nM. In embodiments, the antibody is capable of binding a CD73 antigen with an equilibrium dissociation constant ($K_D$) in this paragraph at a pH below 7.5. In embodiments, the antibody is capable of binding a CD73 antigen with an equilibrium dissociation constant ($K_D$) in this paragraph at a pH of less than about 7.5. In embodiments, the antibody is capable of binding a CD73 antigen with an equilibrium dissociation constant ($K_D$) in this paragraph at a pH of less than about 7.0. In embodiments, the antibody is capable of binding a CD73 antigen with an equilibrium dissociation constant ($K_D$) in this paragraph at a pH of less than about 6.5. In embodiments, the antibody is capable of binding a CD73 antigen with an equilibrium dissociation constant ($K_D$) in this paragraph at a pH of less than about 6.0. In embodiments, the antibody is capable of binding a CD73 antigen with an equilibrium dissociation constant ($K_D$) in this paragraph at a pH of less than about 5.5. In embodiments, the antibody is capable of binding a CD73 antigen with an equilibrium dissociation constant ($K_D$) in this paragraph at a pH of less than about 5. In embodiments, the antibody is capable of binding a CD73 antigen with an equilibrium dissociation constant ($K_D$) in this paragraph at a pH of less than about 4.5. In embodiments, the antibody is capable of binding a CD73 antigen with an equilibrium dissociation constant ($K_D$) in this paragraph at a pH from about 6.0 to about 7.0. In embodiments, the antibody is capable of binding a CD73 antigen with an equilibrium dissociation constant ($K_D$) in this paragraph at a pH of about 6.0. In embodiments, the antibody is capable of binding a CD73 antigen with an equilibrium dissociation constant ($K_D$) in this paragraph at a pH of about 6.1. In embodiments, the antibody is capable of binding a CD73 antigen with an equilibrium dissociation constant ($K_D$) in this paragraph at a pH of about 6.2. In embodiments, the antibody is capable of binding a CD73 antigen with an equilibrium dissociation constant ($K_D$) in this paragraph at a pH of about 6.3. In embodiments, the antibody is capable of binding a CD73 antigen with an equilibrium dissociation constant ($K_D$) in this paragraph at a pH of about 6.4. In embodiments, the antibody is capable of binding a CD73 antigen with an equilibrium dissociation constant ($K_D$) in this paragraph at a pH of about 6.5. In embodiments, the antibody is capable of binding a CD73 antigen with an equilibrium dissociation constant ($K_D$) in this paragraph at a pH of about 6.6. In embodiments, the antibody is capable of binding a CD73 antigen with an equilibrium dissociation constant ($K_D$) in this paragraph at a pH of about 6.7. In embodiments, the antibody is capable of binding a CD73 antigen with an equilibrium dissociation constant ($K_D$) in this paragraph at a pH of about 6.8. In embodiments, the antibody is capable of binding a CD73 antigen with an equilibrium dissociation constant ($K_D$) in this paragraph at a pH of about 6.9. In embodiments, the antibody is capable of binding a CD73 antigen with an equilibrium dissociation constant ($K_D$) in this paragraph at a pH of about 7.0.

In embodiments, the antibody is capable of binding a CD73 antigen with an equilibrium dissociation constant ($K_D$) from about 4.5 to about 25 nM. In embodiments, the antibody is capable of binding a CD73 antigen with an equilibrium dissociation constant ($K_D$) from about 5 to about 25 nM. In embodiments, the antibody is capable of binding a CD73 antigen with an equilibrium dissociation constant ($K_D$) from about 5.5 to about 25 nM. In embodiments, the antibody is capable of binding a CD73 antigen with an equilibrium dissociation constant ($K_D$) from about 6 to about 25 nM. In embodiments, the antibody is capable of binding a CD73 antigen with an equilibrium dissociation constant ($K_D$) from about 6.5 to about 25 nM. In embodiments, the antibody is capable of binding a CD73 antigen with an equilibrium dissociation constant ($K_D$) from about 7 to about 25 nM. In embodiments, the antibody is capable of binding a CD73 antigen with an equilibrium dissociation constant ($K_D$) from about 7.5 to about 25 nM. In embodiments, the antibody is capable of binding a CD73 antigen with an equilibrium dissociation constant ($K_D$) from about 8 to about 25 nM. In embodiments, the antibody is capable of binding a CD73 antigen with an equilibrium dissociation constant ($K_D$) in this paragraph at a pH below 7.5. In embodiments, the antibody is capable of binding a CD73 antigen with an equilibrium dissociation constant ($K_D$) in this paragraph at a pH of less than about 7.5. In embodiments, the antibody is capable of binding a CD73 antigen with an equilibrium dissociation constant ($K_D$) in this paragraph at a pH of less than about 7.0. In embodiments, the antibody is capable of binding a CD73 antigen with an equilibrium dissociation constant ($K_D$) in this paragraph at a pH of less than about 6.5. In embodiments, the antibody is capable of binding a CD73 antigen with an equilibrium dissociation constant ($K_D$) in this paragraph at a pH of less than about 6.0. In embodiments, the antibody is capable of binding a CD73 antigen with an equilibrium dissociation constant ($K_D$) in this paragraph at a pH of less than about 5.5. In embodiments, the antibody is capable of binding a CD73 antigen with an equilibrium dissociation constant ($K_D$) in this paragraph at a pH of less than about 5. In embodiments, the antibody is capable of binding a CD73 antigen with an equilibrium dissociation constant ($K_D$) in this paragraph at a pH of less than about 4.5. In embodiments, the antibody is capable of binding a CD73 antigen with an equilibrium dissociation constant ($K_D$) in this paragraph at a pH from about 6.0 to about 7.0. In embodiments, the antibody is capable of binding a CD73 antigen with an equilibrium dissociation constant ($K_D$) in this paragraph at a pH of about 6.0. In embodiments, the antibody is capable of binding a CD73 antigen with an equilibrium dissociation constant ($K_D$) in this paragraph at a pH of about 6.1. In embodiments, the antibody is capable of binding a CD73 antigen with an equilibrium dissociation constant ($K_D$) in this paragraph at a pH of about 6.2. In embodiments, the antibody is capable of binding a CD73 antigen with an equilibrium dissociation constant ($K_D$) in this paragraph at a pH of about 6.3. In embodiments, the antibody is capable of binding a CD73 antigen with an equilibrium dissociation constant ($K_D$) in this paragraph at a pH of about 6.4. In embodiments, the antibody is capable of binding a CD73 antigen with an equilibrium dissociation constant ($K_D$) in this paragraph at a pH of about 6.5. In embodiments, the antibody is capable of binding a CD73 antigen with an equilibrium dissociation constant ($K_D$) at a pH of about 6.6. In embodiments, the antibody is capable of binding a CD73 antigen with an equilibrium dissociation constant ($K_D$) in this paragraph at a pH of about 6.7. In embodiments, the antibody is capable of binding a CD73 antigen with an equilibrium dissociation constant ($K_D$) in this paragraph at a pH of about 6.8. In embodiments, the antibody is capable of binding a CD73 antigen with an equilibrium dissociation constant ($K_D$) in this paragraph at a pH of about 6.9. In embodiments, the antibody is capable of binding a CD73 antigen with an equilibrium dissociation constant ($K_D$) in this paragraph at a pH of about 7.0.

In embodiments, the antibody is capable of binding a CD73 antigen with an equilibrium dissociation constant ($K_D$) from about 8.5 to about 25 nM. In embodiments, the antibody is capable of binding a CD73 antigen with an equilibrium dissociation constant ($K_D$) from about 9 to about 25 nM. In embodiments, the antibody is capable of binding a CD73 antigen with an equilibrium dissociation constant ($K_D$) from about 9.5 to about 25 nM. In embodiments, the antibody is capable of binding a CD73 antigen with an equilibrium dissociation constant ($K_D$) from about 10 to about 25 nM. In embodiments, the antibody is capable of binding a CD73 antigen with an equilibrium dissociation constant ($K_D$) from about 11 to about 25 nM. In embodiments, the antibody is capable of binding a CD73 antigen with an equilibrium dissociation constant ($K_D$) from about 12 to about 25 nM. In embodiments, the antibody is capable of binding a CD73 antigen with an equilibrium dissociation constant ($K_D$) from about 13 to about 25 nM. In embodiments, the antibody is capable of binding a CD73 antigen with an equilibrium dissociation constant ($K_D$) from about 14 to about 25 nM. In embodiments, the antibody is capable of binding a CD73 antigen with an equilibrium dissociation constant ($K_D$) from about 15 to about 25 nM. In embodiments, the antibody is capable of binding a CD73 antigen with an equilibrium dissociation constant ($K_D$) from about 16 to about 25 nM. In embodiments, the antibody is capable of binding a CD73 antigen with an equilibrium dissociation constant ($K_D$) in this paragraph at a pH below 7.5. In embodiments, the antibody is capable of binding a CD73 antigen with an equilibrium dissociation constant ($K_D$) in this paragraph at a pH of less than about 7.5. In embodiments, the antibody is capable of binding a CD73 antigen with an equilibrium dissociation constant ($K_D$) in this paragraph at a pH of less than about 7.0. In embodiments, the antibody is capable of binding a CD73 antigen with an equilibrium dissociation constant ($K_D$) in this paragraph at a pH of less than about 6.5. In embodiments, the antibody is capable of binding a CD73 antigen with an equilibrium dissociation constant ($K_D$) in this paragraph at a pH of less than about 6.0. In embodiments, the antibody is capable of binding a CD73 antigen with an equilibrium dissociation constant ($K_D$) in this paragraph at a pH of less than about 5.5. In embodiments, the antibody is capable of binding a CD73 antigen with an equilibrium dissociation constant ($K_D$) in this paragraph at a pH of less than about 5. In embodiments, the antibody is capable of binding a CD73 antigen with an equilibrium dissociation constant ($K_D$) in this paragraph at a pH of less than about 4.5. In embodiments, the antibody is capable of binding a CD73 antigen with an equilibrium dissociation constant ($K_D$) in this paragraph at a pH from about 6.0 to about 7.0. In embodiments, the antibody is capable of binding a CD73 antigen with an equilibrium dissociation constant ($K_D$) in this paragraph at a pH of about 6.0. In embodiments, the antibody is capable of binding a CD73 antigen with an equilibrium dissociation constant ($K_D$) in this paragraph at a pH of about 6.1. In embodiments, the antibody is capable of binding a CD73 antigen with an equilibrium dissociation constant ($K_D$) in this paragraph at a pH of about 6.2. In embodiments, the antibody is capable of binding a CD73 antigen with an equilibrium dissociation constant ($K_D$) in this paragraph at a pH of about 6.3. In embodiments, the antibody is capable of binding a CD73 antigen with an equilibrium dissociation constant ($K_D$) in this paragraph at a pH of about 6.4. In embodiments, the antibody is capable of binding a CD73 antigen with an equilibrium dissociation constant ($K_D$) in this paragraph at a pH of about 6.5. In embodiments, the antibody is capable of binding a CD73 antigen with an equilibrium dissociation constant ($K_D$) in this paragraph at a pH of about 6.6. In embodiments, the antibody is capable of binding a CD73 antigen with an equilibrium dissociation constant ($K_D$) in this paragraph at a pH of about 6.7. In embodiments, the antibody is capable of binding a CD73 antigen with an equilibrium dissociation constant ($K_D$) in this paragraph at a pH of about 6.8. In embodiments, the antibody is capable of binding a CD73 antigen with an equilibrium dissociation constant ($K_D$) in this paragraph at a pH of about 6.9. In embodiments, the antibody is capable of binding a CD73 antigen with an equilibrium dissociation constant ($K_D$) in this paragraph at a pH of about 7.0.

In embodiments, the antibody is capable of binding a CD73 antigen with an equilibrium dissociation constant ($K_D$) from about 17 to about 25 nM. In embodiments, the antibody is capable of binding a CD73 antigen with an equilibrium dissociation constant ($K_D$) from about 18 to about 25 nM. In embodiments, the antibody is capable of binding a CD73 antigen with an equilibrium dissociation constant ($K_D$) from about 19 to about 25 nM. In embodiments, the antibody is capable of binding a CD73 antigen with an equilibrium dissociation constant ($K_D$) from about 20 to about 25 nM. In embodiments, the antibody is capable of binding a CD73 antigen with an equilibrium dissociation constant ($K_D$) from about 21 to about 25 nM. In embodiments, the antibody is capable of binding a CD73 antigen with an equilibrium dissociation constant ($K_D$) from about 22 to about 25 nM. In embodiments, the antibody is capable of binding a CD73 antigen with an equilibrium dissociation constant ($K_D$) from about 23 to about 25 nM. In embodiments, the antibody is capable of binding a CD73 antigen with an equilibrium dissociation constant ($K_D$) from about 24 to about 25 nM. In embodiments, the antibody is capable of binding a CD73 antigen with an equilibrium dissociation constant ($K_D$) of about 0.5, 1, 2, 3, 4, 5, 6, 7, 8, 9, 10, 11, 12, 13, 14, 15, 16, 17, 18, 19, 20, 21, 22, 23, 24, or 25 nM. In embodiments, the antibody is capable of binding a CD73 antigen with an equilibrium dissociation constant ($K_D$) in this paragraph at a pH below 7.5. In embodiments, the antibody is capable of binding a CD73 antigen with an equilibrium dissociation constant ($K_D$) in this paragraph at a pH of less than about 7.5. In embodiments, the antibody is capable of binding a CD73 antigen with an equilibrium dissociation constant ($K_D$) in this paragraph at a pH of less than about 7.0. In embodiments, the antibody is capable of binding a CD73 antigen with an equilibrium dissociation constant ($K_D$) in this paragraph at a pH of less than about 6.5. In embodiments, the antibody is capable of binding a CD73 antigen with an equilibrium dissociation constant ($K_D$) in this paragraph at a pH of less than about 6.0. In embodiments, the antibody is capable of binding a CD73 antigen with an equilibrium dissociation constant ($K_D$) in this paragraph at a pH of less than about 5.5. In embodiments, the antibody is capable of binding a CD73 antigen with an equilibrium dissociation constant ($K_D$) in this paragraph at a pH of less than about 5. In embodiments, the antibody is capable of binding a CD73 antigen with an equilibrium dissociation constant ($K_D$) in this paragraph at a pH of less than about 4.5. In embodiments, the antibody is capable of binding a CD73 antigen with an equilibrium dissociation constant ($K_D$) in this paragraph at a pH from about 6.0 to about 7.0. In embodiments, the antibody is capable of binding a CD73 antigen with an equilibrium dissociation constant ($K_D$) in this paragraph at a pH of about 6.0. In embodiments, the antibody is capable of binding a CD73 antigen with an equilibrium dissociation constant ($K_D$) in this paragraph at a pH of about 6.1. In embodiments, the antibody is capable of binding a CD73 antigen with an equilibrium dissociation constant ($K_D$) in this paragraph at a pH of about 6.2. In embodiments, the antibody is capable of binding a CD73 antigen with an equilibrium dissociation constant ($K_D$) in this paragraph at a pH of about 6.3. In embodiments, the antibody is capable of binding a CD73 antigen with an equilibrium dissociation constant ($K_D$) in this paragraph at a pH of about 6.4. In embodiments, the antibody is capable of binding a CD73 antigen with an equilibrium dissociation constant ($K_D$) in this paragraph at a pH of about 6.5. In embodiments, the antibody is capable of binding a CD73 antigen with an equilibrium dissociation constant ($K_D$) in this paragraph at a pH of about 6.6. In embodiments, the antibody is capable of binding a CD73 antigen with an equilibrium dissociation constant ($K_D$) in this paragraph at a pH of about 6.7. In embodiments, the antibody is capable of binding a CD73 antigen with an equilibrium dissociation constant ($K_D$) in this paragraph at a pH of about 6.8. In embodiments, the antibody is capable of binding a CD73 antigen with an equilibrium dissociation constant ($K_D$) in this paragraph at a pH of about 6.9. In embodiments, the antibody is capable of binding a CD73 antigen with an equilibrium dissociation constant ($K_D$) in this paragraph at a pH of about 7.0.

In embodiments, the antibody is capable of binding a CD73 antigen with an equilibrium dissociation constant ($K_D$) of about 7.1 nM. In embodiments, the antibody is capable of binding a CD73 antigen with an equilibrium dissociation constant ($K_D$) of about 6.9 nM. In embodiments, the antibody is capable of binding a CD73 antigen with an equilibrium dissociation constant ($K_D$) of about 9.4 nM. In embodiments, the antibody is capable of binding a CD73 antigen with an equilibrium dissociation constant ($K_D$) of about 19.5 nM. In embodiments, the antibody is capable of binding a CD73 antigen with an equilibrium dissociation constant ($K_D$) of about 17.8 nM. In embodiments, the antibody is capable of binding a CD73 antigen with an equilibrium dissociation constant ($K_D$) of about 15.9 nM. In embodiments, the antibody is capable of binding a CD73 antigen with an equilibrium dissociation constant ($K_D$) in this paragraph at a pH below 7.5. In embodiments, the antibody is capable of binding a CD73 antigen with an equilibrium dissociation constant ($K_D$) in this paragraph at a pH of less than about 7.5. In embodiments, the antibody is capable of binding a CD73 antigen with an equilibrium dissociation constant ($K_D$) in this paragraph at a pH of less than about 7.0. In embodiments, the antibody is capable of binding a CD73 antigen with an equilibrium dissociation constant ($K_D$) in this paragraph at a pH of less than about 6.5. In embodiments, the antibody is capable of binding a CD73 antigen with an equilibrium dissociation constant ($K_D$) in this paragraph at a pH of less than about 6.0. In embodiments, the antibody is capable of binding a CD73 antigen with an equilibrium dissociation constant ($K_D$) in this paragraph at a pH of less than about 5.5. In embodiments, the antibody is capable of binding a CD73 antigen with an equilibrium dissociation constant ($K_D$) in this paragraph at a pH of less than about 5. In embodiments, the antibody is capable of binding a CD73 antigen with an equilibrium dissociation constant ($K_D$) in this paragraph at a pH of less than about 4.5. In embodiments, the antibody is capable of binding a CD73 antigen with an equilibrium dissociation constant ($K_D$) in this paragraph at a pH from about 6.0 to about 7.0. In embodiments, the antibody is capable of binding a CD73 antigen with an equilibrium dissociation constant ($K_D$) in this paragraph at a pH of about 6.0. In embodiments, the antibody is capable of binding a CD73 antigen with an equilibrium dissociation constant ($K_D$) in this paragraph at a pH of about 6.1. In embodiments, the antibody is capable of binding a CD73 antigen with an equilibrium dissociation constant ($K_D$) in this paragraph at a pH of about 6.2. In embodiments, the antibody is capable of binding a CD73 antigen with an equilibrium dissociation constant ($K_D$) in this paragraph at a pH of about 6.3. In embodiments, the antibody is capable of binding a CD73 antigen with an equilibrium dissociation constant ($K_D$) in this paragraph at a pH of about 6.4. In embodiments, the antibody is capable of binding a CD73 antigen with an equilibrium dissociation constant ($K_D$) in this paragraph at a pH of about 6.5. In embodiments, the antibody is capable of binding a CD73 antigen with an equilibrium dissociation constant ($K_D$) in this paragraph at a pH of about 6.6. In embodiments, the antibody is capable of binding a CD73 antigen with an equilibrium dissociation constant ($K_D$) in this paragraph at a pH of about 6.7. In embodiments, the antibody is capable of binding a CD73 antigen with an equilibrium dissociation constant ($K_D$) in this paragraph at a pH of about 6.8. In embodiments, the antibody is capable of binding a CD73 antigen with an equilibrium dissociation constant ($K_D$) in this paragraph at a pH of about 6.9. In embodiments, the antibody is capable of binding a CD73 antigen with an equilibrium dissociation constant ($K_D$) in this paragraph at a pH of about 7.0.

In one aspect, an antibody capable of binding CD73 at a pH of less than about 7.5 is provided. In embodiments, the antibody, is capable of binding a CD73 antigen at a pH of less than about 7.0. In embodiments, the antibody, is capable of binding a CD73 antigen at a pH of less than about 6.5. In embodiments, the antibody, is capable of binding a CD73 antigen at a pH of less than about 6.0. In embodiments, the antibody, is capable of binding a CD73 antigen at a pH of less than about 5.5. In embodiments, the antibody, is capable of binding a CD73 antigen at a pH of less than about 5. In embodiments, the antibody, is capable of binding a CD73 antigen at a pH of less than about 4.5. In embodiments, the antibody is capable of binding a CD73 antigen at a pH from about 6.0 to about 7.0. In embodiments, the antibody is capable of binding a CD73 antigen at a pH of about 6.0. In embodiments, the antibody is capable of binding a CD73 antigen at a pH of about 6.1. In embodiments, the antibody is capable of binding a CD73 antigen at a pH of about 6.2. In embodiments, the antibody is capable of binding a CD73 antigen at a pH of about 6.3. In embodiments, the antibody is capable of binding a CD73 antigen at a pH of about 6.4. In embodiments, the antibody is capable of binding a CD73 antigen at a pH of about 6.5. In embodiments, the antibody is capable of binding a CD73 antigen at a pH of about 6.6. In embodiments, the antibody is capable of binding a CD73 antigen at a pH of about 6.7. In embodiments, the antibody is capable of binding a CD73 antigen at a pH of about 6.8. In embodiments, the antibody is capable of binding a CD73 antigen at a pH of about 6.9. In embodiments, the antibody is capable of binding a CD73 antigen at a pH of about 7.0.

In embodiments, the antibody as set forth in this paragraph is a humanized antibody. In embodiments, the antibody includes (i) a CDR L1 of SEQ ID NO:1 and (ii) an amino acid substitution selected from the group consisting of: (a) any amino acid other than asparagine at a position corresponding to Kabat position 27A of SEQ ID NO:1; (b) any amino acid other than valine at a position corresponding to Kabat position 27B of SEQ ID NO:1; or (c) any amino acid other than serine at a position corresponding to Kabat position 27C of SEQ ID NO:1.

The anti-CD73 antibody provided herein including embodiments thereof may include a glutamine at a position corresponding to Kabat position 297.

In embodiments, the anti-CD73 antibody is bound to a CD73 antigen. In embodiments, the CD73 antigen forms part of a cell. In embodiments, the cell is a lymphoid cell. In embodiments, the cell is a T cell. In embodiments, the cell is a cancer cell.

In one aspect, an antibody bound to a CD73 antigen at a pH of less than about 7.5 is provided. In embodiments, the antibody includes (i) a CDR L1 of SEQ ID NO:1 and (ii) an amino acid substitution selected from the group consisting of: (a) any amino acid other than asparagine at a position corresponding to Kabat position 27A of SEQ ID NO:1; (b) any amino acid other than valine at a position corresponding to Kabat position 27B of SEQ ID NO:1; or (c) any amino acid other than serine at a position corresponding to Kabat position 27C of SEQ ID NO:1.

In another aspect, a non-glycosylated antibody (e.g., anti-CD73 antibody) is provided. The non-glycosylated antibody binds the same epitope as a 1E9 antibody, wherein the 1E9 antibody includes a humanized light chain variable region including a mouse CDR L1, mouse CDR L2, or mouse CDR L3 and a humanized heavy chain variable region including a mouse CDR H1, mouse CDR H2, or mouse CDR H3.

In another aspect a non-glycosylated antibody (e.g., anti-CD73 antibody) is provided. The non-glycosylated antibody (e.g., anti-CD73 antibody) binds the same epitope as a 1E9 antibody, wherein the 1E9 antibody includes a humanized light chain variable region and a humanized heavy chain variable region. The humanized light chain variable region includes:

(i) a mouse CDR L1 as set forth in SEQ ID NO:1, a mouse CDR L2 as set forth in SEQ ID NO:2, a mouse CDR L3 as set forth in SEQ ID NO:3 and (ii) a valine at a position corresponding to Kabat position 2, a methionine at a position corresponding to Kabat position 4, an aspartic acid or a leucine at a position corresponding to Kabat position 9, a proline or a serine at a position corresponding to Kabat position 12, a lysine or a proline at a position corresponding to Kabat position 18, a alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a leucine at a position corresponding to Kabat position 78, a serine or an alanine at a position corresponding to Kabat position 80, a glutamine at a position corresponding to Kabat position 100, a valine at a position corresponding to Kabat position 104, a glutamic acid or an alanine at a position corresponding to Kabat position 1, a glutamine at a position corresponding to Kabat position 3, a phenylalanine or a threonine at a position corresponding to Kabat position 10, a glutamine at a position corresponding to Kabat position 11, an alanine or a leucine at a position corresponding to Kabat position 13, a threonine at a position corresponding to Kabat position 14, a valine or a proline at a position corresponding to Kabat position 15, a lysine at a position corresponding to Kabat position 16, a glutamic acid or an aspartic acid at a position corresponding to Kabat position 17, a threonine at a position corresponding to Kabat position 22, a lysine at a position corresponding to Kabat position 42, an arginine at a position corresponding to Kabat position 45, an isoleucine at a position corresponding to Kabat position 58, a tyrosine at a position corresponding to Kabat position 67, a phenylalanine at a position corresponding to Kabat position 73, an isoleucine at a position corresponding to Kabat position 78, a tyrosine at a position corresponding to Kabat position 85, or a phenylalanine at a position corresponding to Kabat position 87. The humanized heavy chain variable region includes:

(i) a mouse CDR H1 as set forth in SEQ ID NO:4, a mouse CDR H2 as set forth in SEQ ID NO:5, and a mouse CDR H3 as set forth in SEQ ID NO:6 and
(ii) an isoleucine at a position corresponding to Kabat position 37, an alanine or a proline at a position corresponding to Kabat position 40, a lysine at a position corresponding to Kabat position 43, a serine at a position corresponding to Kabat position 70, an isoleucine or a threonine at a position corresponding to Kabat position 75, a tryptophan at a position corresponding to Kabat position 82, an arginine or a lysine at a position corresponding to Kabat position 83, a alanine at a position corresponding to Kabat position 84, a serine at a position corresponding to Kabat position 85, a valine or a methionine at a position corresponding to Kabat position 89, a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, a threonine at a position corresponding to Kabat position 87, a glutamic acid at a position corresponding to Kabat position 1, a valine at a position corresponding to Kabat position 24, a arginine at a position corresponding to Kabat position 44, a methionine at a position corresponding to Kabat position 48, a leucine at a position corresponding to Kabat position 80, or a glutamic acid at a position corresponding to Kabat position 81.

Nucleic Acid Compositions

In one aspect, an isolated nucleic acid encoding an anti-CD73 antibody provided herein including embodiments thereof is provided. The anti-CD73 antibody encoded by the isolated nucleic acid is described in detail throughout this application (including the description above and in the examples section). Thus, the anti-CD73 encoded by the isolated nucleic acid includes all of the embodiments described herein. For example, the nucleic acid may encode a CDR L1 of SEQ ID NO:1 and an amino acid substitution at a position corresponding to Kabat position 27A, 27B or 27C of SEQ ID NO:1. For instance, the nucleic acid may encode a CDR L1 of SEQ ID NO:1 and a proline at a position corresponding to Kabat position 27B of SEQ ID NO:1.

In embodiments, the isolated nucleic acid includes the sequence of SEQ ID NO:10, SEQ ID NO:11 or SEQ ID NO:12. In embodiments, the isolated nucleic acid includes the sequence of SEQ ID NO:10. In embodiments, the isolated nucleic acid includes the sequence of SEQ ID NO:11. In embodiments, the isolated nucleic acid includes the sequence of SEQ ID NO:12. In embodiments, the isolated nucleic acid includes the sequence of SEQ ID NO:10 and SEQ ID NO: 12. In embodiments, the isolated nucleic acid includes the sequence of SEQ ID NO:11 and SEQ ID NO:12. In embodiments, the isolated nucleic acid includes the sequence of SEQ ID NO:28. In embodiments, the nucleic acid forms part of a cell.

In embodiments, the nucleic acid includes a codon-optimized sequence. In embodiments, the nucleic acid includes the sequence of SEQ ID NO:24 or SEQ ID NO:25. In embodiments, the nucleic acid includes the sequence of SEQ ID NO:24 and SEQ ID NO:25. In embodiments, the nucleic acid includes the sequence of SEQ ID NO:24. In embodiments, the nucleic acid includes the sequence of SEQ ID NO:25. In embodiments, the nucleic acid is the sequence of SEQ ID NO:24 or SEQ ID NO:25. In embodiments, the nucleic acid is the sequence of SEQ ID NO:24 and SEQ ID NO:25. In embodiments, the nucleic acid is the sequence of SEQ ID NO:24. In embodiments, the nucleic acid is the sequence of SEQ ID NO:25.

Pharmaceutical Compositions

In another aspect, a pharmaceutical composition including a therapeutically effective amount of a non-glycosylated antibody (e.g. an anti-CD73 antibody) provided herein including embodiments thereof and a pharmaceutically acceptable excipient is provided.

In another aspect, a pharmaceutical composition including a therapeutically effective amount of an anti-CD73 antibody provided herein including embodiments thereof and a pharmaceutically acceptable excipient is provided.

A therapeutically effective amount as provided herein refers to an amount effective to achieve its intended purpose. The actual amount effective for a particular application will depend, inter alia, on the condition being treated. When administered in methods to treat a disease, the pharmaceutical compositions described herein will contain an amount of active anti-CD73 antibody effective to achieve the desired result, e.g., modulating the activity of a target molecule (e.g., CD73), and/or reducing, eliminating, or slowing the progression of disease symptoms (e.g., cancer). Determination of a therapeutically effective amount of an anti-CD73 antibody provided herein is well within the capabilities of those skilled in the art, especially in light of the detailed disclosure herein.

Acceptable carriers, excipients or stabilizers are nontoxic to recipients at the dosages and concentrations employed, and include buffers such as phosphate, citrate, or acetate at a pH typically of 5.0 to 8.0, most often 6.0 to 7.0; salts such as sodium chloride, potassium chloride, etc. to make isotonic; antioxidants, preservatives, low molecular weight polypeptides, proteins, hydrophilic polymers such as polysorbate 80, amino acids such as glycine, carbohydrates, chelating agents, sugars, and other standard ingredients known to those skilled in the art (Remington's Pharmaceutical Science $16^{th}$ edition, Osol, A. Ed. 1980). The mAb is typically present at a concentration of 0.1-100 mg/ml, e.g., 1-10 mg/ml or 10-50 mg/ml, for example 5, 10, 20, 30, 40, 50 or 60 mg/ml.

A pharmaceutical composition including an anti-CD73 antibody as described herein can be administered by a variety of methods known in the art. The route and/or mode of administration vary depending upon the desired results. In embodiments, administration is intravenous, intramuscular, intraperitoneal, or subcutaneous, or administered proximal to the site of the target. Pharmaceutically acceptable excipients can be suitable for intravenous, intramuscular, subcutaneous, parenteral, spinal or epidermal administration (e.g., by injection or infusion).

Pharmaceutical compositions of the anti-CD73 antibody can be prepared in accordance with methods well known and routinely practiced in the art. See, e.g., *Remington: The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Typically, a therapeutically effective dose or efficacious dose of the anti-CD73 antibody is employed in the pharmaceutical compositions of the invention. The anti-CD73 antibodies provided can be formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It may be advantageous to formulate the anti-CD73 antibodies in combination with other therapies or agents. It can be advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of anti-CD73 antibody calculated to produce the desired therapeutic effect in association with the required pharmaceutical excipient.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, the route of administration, the time of administration, the rate of excretion of the particular antibody being employed, the duration of the treatment, other drugs, compounds and/or materials used in combination with the particular compositions employed, the age, sex, weight, condition, general health and prior medical history of the patient being treated, and like factors.

A physician or veterinarian can start doses of the anti-CD73 antibodies of the invention employed in the pharmaceutical composition at levels lower than that required achieving the desired therapeutic effect and gradually increase the dosage until the desired effect is achieved. In general, effective doses of the compositions of the present invention vary depending upon many different factors, including the specific disease or condition to be treated, means of administration, target site, physiological state of the patient, whether the patient is human or an animal, other medications administered, and whether treatment is prophylactic or therapeutic. Treatment dosages need to be titrated to optimize safety and efficacy. For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months.

The anti-CD73 antibody provided herein can be administered on multiple occasions. Intervals between single dosages can be weekly, monthly or yearly. Intervals can also be irregular as indicated by measuring blood levels of the anti-CD73 antibody in the patient. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, anti-CD73 antibodies show longer half-life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Methods

In one aspect, a method of treating cancer in a subject in need thereof is provided. The method includes administering to the subject a therapeutically effective amount of a non-glycosylated antibody (e.g. an anti-CD73 antibody) provided herein including embodiments thereof, thereby treating cancer in the subject.

In one aspect, a method of treating cancer in a subject in need thereof is provided. The method includes administering to the subject a therapeutically effective amount of an anti-CD73 antibody provided herein including embodiments thereof, thereby treating cancer in the subject. In embodiments, the cancer is a lymphoid cancer.

Methods of Inhibition

In one aspect, a method of inhibiting proliferation of a cell is provided. The method includes (i) contacting a cell with an anti-CD73 antibody as provided herein including embodiments thereof, thereby forming a contacted cell. (ii) The anti-CD73 antibody is allowed to bind a CD73 antigen on the contacted cell, thereby inhibiting proliferation of the cell. In embodiments, the cell is a lymphoid cell. In embodiments, the lymphoid cell is a T cell.

In one aspect, a method of inhibiting proliferation of a cell is provided. The method includes (i) contacting a cell with a non-glycosylated antibody as provided herein including embodiments thereof, thereby forming a contacted cell. (ii) The non-glycosylated antibody is allowed to bind a CD73 antigen on the contacted cell, thereby inhibiting proliferation of the cell. In embodiments, the cell is a lymphoid cell. In embodiments, the lymphoid cell is a T cell.

Methods of Detecting

In one aspect, a method of detecting an anti-CD73 antibody bound to a CD73 antigen is provided. The method includes, (i) contacting an anti-CD73 antibody with a CD73 antigen at a pH of less than about 7.5 and (ii) detecting binding of the anti-CD73 antibody to the CD73 antigen. In embodiments, the pH is from about 6.0 to about 7.0. In embodiments, the pH is about 6.7. in embodiments, the pH is about 6.3. In embodiments, the detecting binding of step (ii) includes detecting inhibition of CD73 catalytic activity. In embodiments, the CD73 antigen forms part of a cell. In embodiments, the CD73 antigen is bound to a solid support. In embodiments, the anti-CD73 antibody includes a detectable moiety.

Methods of T-Cell Activation

Provided herein are methods of activating an immunosuppressed (non-activated, non-proliferating) T cell in a cancer environment. Thus, in one aspect a method of activating an immunosuppressed T cell is provided. The method includes, (i) contacting a T cell with an anti-CD73 antibody as provided herein including embodiments thereof, thereby forming a contacted T cell. (ii) The anti-CD73 antibody is allowed to bind a CD73 antigen on the contacted T cell, thereby activating the immunosuppressed T cell. In embodiments, the T cell is in a cancer environment. In embodiments, the IFN-gamma secretion of the contacted T cell is increased relative to the absence of the antibody. In embodiments, the proliferation of the contacted T cell is increased relative to the absence of the antibody. An "immunosuppressed T cell" as provided herein is a T cell residing in a cancer environment (in the close vicinity to and/or in physiological contact with a cancer cell or solid tumor), which does not proliferate or secrete detectable amounts of cytokines or express cell surface markers characteristic of activated T cells (e.g., IFN-gamma, CD25, CD38).

Combination Treatment Methods

The methods of treating provided herein including embodiments thereof, may include administration of a second therapeutic agent. Therefore, the methods of treatment as provided herein include administering an anti-CD73 antibody as provided herein or a non-glycosylated antibody as provided herein in combination with a second therapeutic agent. The second therapeutic agent may be any composition useful in treating or preventing cancer.

In one aspect, a method of treating cancer in a subject in need thereof is provided. The method includes administering to the subject a therapeutically effective amount of an anti-CD73 antibody provided herein including embodiments thereof and an effective amount of a second therapeutic agent, thereby treating cancer in the subject.

In one aspect, a method of treating cancer in a subject in need thereof is provided. The method includes administering to the subject a therapeutically effective amount of a non-glycosylated antibody provided herein including embodiments thereof and an effective amount of a second therapeutic agent, thereby treating cancer in the subject.

The second therapeutic agent useful for the methods provided herein may be a compound, drug, antagonist, inhibitor, or modulator, having antineoplastic properties or the ability to inhibit the growth or proliferation of cells. In embodiments, the second therapeutic agent is a chemotherapeutic. "Chemotherapeutic" or "chemotherapeutic agent" is used in accordance with its plain ordinary meaning and refers to a chemical composition or compound having antineoplastic properties or the ability to inhibit the growth or proliferation of cells. In embodiments, the second therapeutic agent is radiation therapy. In embodiments, the second therapeutic agent is an agent approved by the FDA or similar regulatory agency of a country other than the USA, for treating cancer.

In embodiments, the second therapeutic agent is a compound. In embodiments, the compound is a purine receptor antagonist. In embodiments, the compound is an $A_{2A}$ adenosine receptor antagonist or $A_{2B}$ adenosine receptor antagonist. In embodiments, the compound is an $A_{2A}$ adenosine receptor antagonist. In embodiments, the compound is an $A_{2B}$ adenosine receptor antagonist. In embodiments, the compound is any one of the compounds disclosed in U.S. Pat. Nos. 9,120,807, 8,450,328 or 8,354,415, which are hereby incorporated by reference and for all purposes. In embodiments, the compound is a thienopyrimidine compound. In embodiments, the A2A adenosine receptor antagonist is compound CPI-444. In embodiments, compound CPI-444 has the structure:

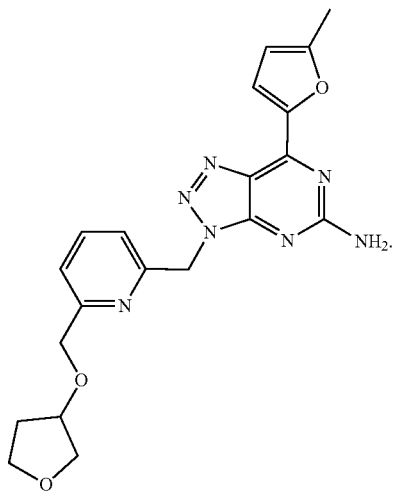 [SMILES: Cc1ccc(-c2nc(N)nc3c2nnn3Cc2cccc(COC3CCOC3)n2)o1]

In embodiments, the $A_{2A}$ adenosine receptor antagonist (e.g. CPI-444) has the structure:

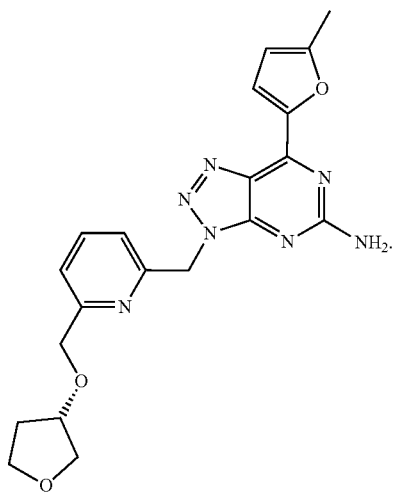

In embodiments, the $A_{2A}$ adenosine receptor antagonist has the structure:

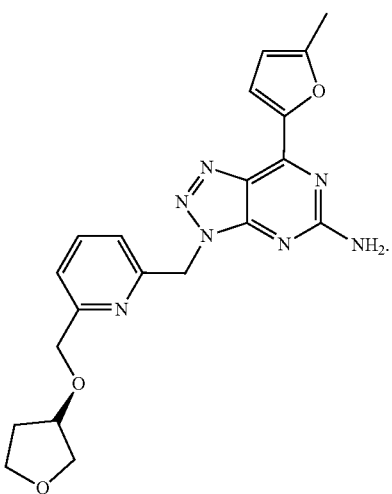

In embodiments, the $A_{2A}$ adenosine receptor antagonist has the structure of formula:

(I)

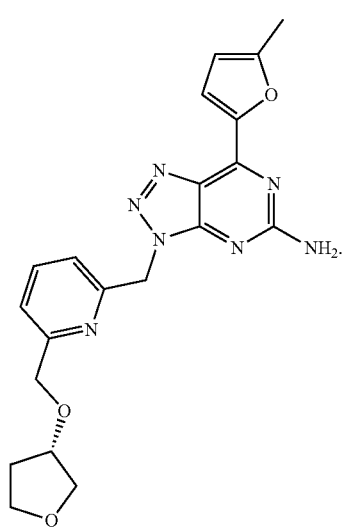

$C_{20}H_{21}N_7O_3$
Mol. Wt.: 407.43

The term "$A_{2A}$ adenosine receptor" as provided herein includes any of the recombinant or naturally-occurring forms of the $A_{2A}$ adenosine receptor (ADORA2A) or variants or homologs thereof that maintain ADORA2A protein activity (e.g. within at least 50%, 80%, 90%, 95%, 96%, 97%, 98%, 99% or 100% activity compared to ADORA2A). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ADORA2A polypeptide. In embodiments, ADORA2A is the protein as identified by the NCBI sequence reference GI:5921992, homolog or functional fragment thereof.

The term "A2B adenosine receptor" as provided herein includes any of the recombinant or naturally-occurring forms of the $A_{2B}$ adenosine receptor (ADORA2B) or variants or homologs thereof that maintain ADORA2B protein activity (e.g. within at least 50%, 80%, 90%, 95%, 96%, 97%, 98%, 99% or 100% activity compared to ADORA2B). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ADORA2B polypeptide. In embodiments, ADORA2B is the protein as identified by the NCBI sequence reference GI:4501951, homolog or functional fragment thereof.

In embodiments, the therapeutic agent is a humanized antibody. In embodiments, the humanized antibody is an antibody capable of binding protein programmed cell death ligand 1 (PD-L1). embodiments, the second antibody is atezolizumab. In embodiments, the second antibody is an antibody capable of binding protein programmed cell death protein 1 (PD-1). In embodiments, the second antibody is an antibody capable of binding CTLA-4.

The term "atezolizumab" or "MPDL3280A" refers a fully humanized, engineered monoclonal antibody of IgG1 isotype against the protein programmed cell death ligand 1 (PD-L1). In the customary sense, atezolizumab refers to CAS Registry number 1380723-44-3.

The term "PDL-1" as provided herein includes any of the recombinant or naturally-occurring forms of the protein programmed cell death ligand 1 (PD-L1) or variants or homologs thereof that maintain PDL-1 protein activity (e.g. within at least 50%, 80%, 90%, 95%, 96%, 97%, 98%, 99% or 100% activity compared to PDL-1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PDL-1 polypeptide. In embodiments, PDL-1 is the protein as identified by the NCBI sequence reference GI:390979639, homolog or functional fragment thereof.

The term "PD-1" as provided herein includes any of the recombinant or naturally-occurring forms of the protein programmed cell death protein 1 (PD-1) or variants or homologs thereof that maintain PD-1 protein activity (e.g. within at least 50%, 80%, 90%, 95%, 96%, 97%, 98%, 99% or 100% activity compared to PD-1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-1 polypeptide. In embodiments, PD-1 is the protein as identified by the NCBI sequence reference GI:167857792, homolog or functional fragment thereof.

The term "CTLA-4" or "CTLA-4 protein" as provided herein includes any of the recombinant or naturally-occurring forms of the cytotoxic T-lymphocyte-associated protein 4 (CTLA-4) or variants or homologs thereof that maintain CTLA-4 protein activity (e.g. within at least 50%, 80%, 90%, 95%, 96%, 97%, 98%, 99% or 100% activity compared to CTLA-4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTLA-4 polypeptide. In embodiments, CTLA-4 is the protein as identified by the NCBI sequence reference GI:83700231, homolog or functional fragment thereof.

In the provided methods of treatment, additional therapeutic agents can be used that are suitable to the disease (e.g., cancer) being treated. Thus, in some embodiments, the provided methods of treatment further include administering a second therapeutic agent to the subject. Suitable additional therapeutic agents include, but are not limited to analgesics, anesthetics, analeptics, corticosteroids, anticholinergic agents, anticholinesterases, anticonvulsants, antineoplastic agents, allosteric inhibitors, anabolic steroids, antirheumatic agents, psychotherapeutic agents, neural blocking agents, anti-inflammatory agents, antihelmintics, antibiotics, anticoagulants, antifungals, antihistamines, antimuscarinic agents, antimycobacterial agents, antiprotozoal agents, antiviral agents, dopaminergics, hematological agents, immunological agents, muscarinics, protease inhibitors, vitamins, growth factors, and hormones. The choice of agent and dosage can be determined readily by one of skill in the art based on the given disease being treated.

Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

According to the methods provided herein, the subject is administered an effective amount of one or more of the therapeutic agents provided herein (i.e. anti-CD73 antibody in combination with, for example, a compound or a second antibody). The terms effective amount and effective dosage are used interchangeably. The term effective amount is defined as any amount necessary to produce a desired physiologic response (e.g., reduction of inflammation). Effective amounts and schedules for administering the agent may be determined empirically by one skilled in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

Examples

In FIG. 1 antibodies were treated with PNGase F or mock treated (no enzyme) overnight at 37 C. Removal of N-linked glycosylation with PNGase F reduced the size of the light chain in treated samples to 25 kDa, consistent with IgG1 isotype control (lane 5). Analogous results with CPX-006 (light chain of SEQ ID NO:13 and heavy chain of SEQ ID NO:14) (lanes 2-4) and 1E9-mIgG3 (light chain variable region of SEQ ID NO:17 and heavy chain variable region of SEQ ID NO:18) (lanes 6-8) confirm that the glycosylation site is in the CDR as CPX-006 and 1E9-mIgG3 contain the same CDRs but different frameworks.

Figure 2:
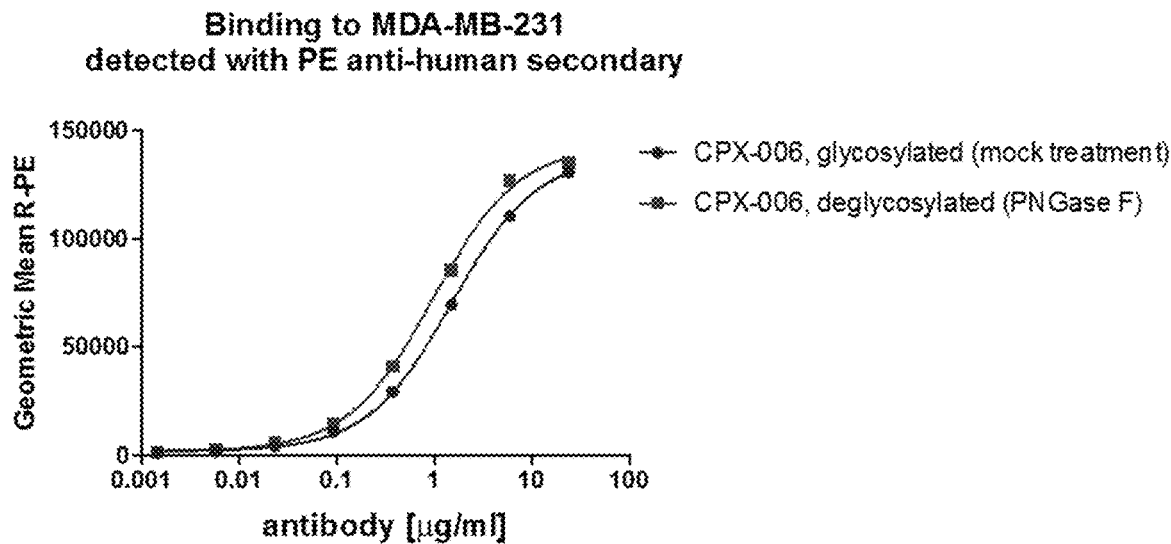
FIG. 2: Deglycosylated anti-CD73 Antibodies Bind to Cellular CD73 with Similar Potency as Glycosylated Antibody.

In FIG. 2 binding of CPX-006 (light chain of SEQ ID NO:13 and heavy chain of SEQ ID NO:14) (glycosylated) or CPX-006 that was deglycosylated enzymatically with PNGase F was assessed by flow cytometry. MDA-MB-231, a human breast cancer cell line, was incubated with the indicated antibodies over a range of concentrations. Antibody binding was detected with PE anti-human secondary and flow cytometry analysis.

Figure 3:
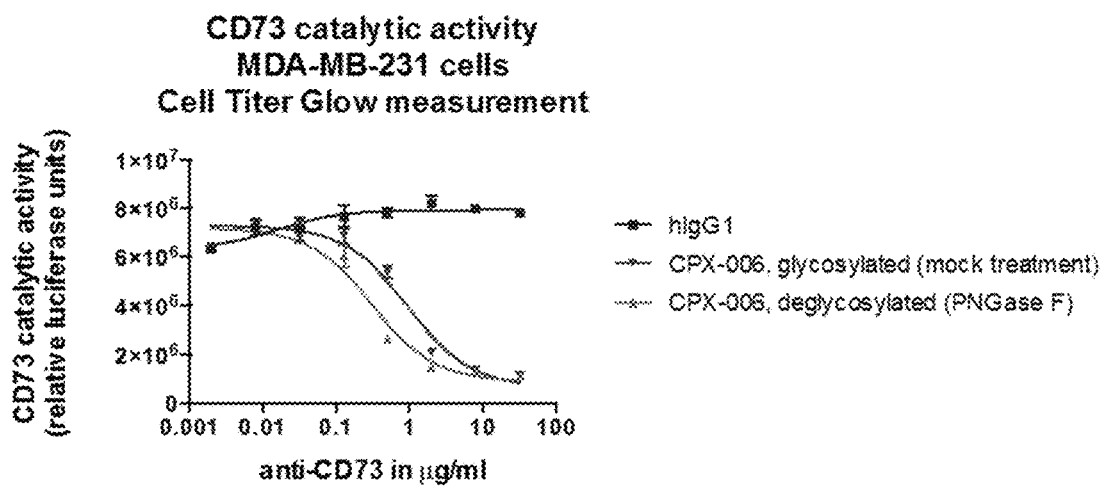
FIG. 3: Deglycosylated CPX-006 Inhibits CD73 Activity with Similar Potency as Glycosylated Antibody.

In FIG. 3 MDA-MB-231, a human breast cancer cell line, was incubated with the indicated antibodies over a range of concentrations. CD73 activity was measured as described in PMID: 22522649.

Table 1: CDR L1 was modified as indicated at sites encoding amino acids at Kabat position 27A or 27C. The original CDR (CDR L1 of SEQ ID NO:1), which is included in CPX-006 (SEQ ID NO:8), is included as a reference and represents the parental sequence. For CPX-008 (SEQ ID NO:19), CPX-009 (SEQ ID NO:20), CPX-011 (SEQ ID NO:21), and CPX-014 (SEQ ID NO:23), substitutions were made in plasmids encoding the CPX-006 light chain (SEQ ID NO:8). For CPX-012 (SEQ ID NO:22), substitution was made in a plasmid encoding the CPX-005 light chain SEQ ID NO:7). CPX-006 and CPX-005 differ in their framework regions.

| Identifier | Amino Acid at Kabat 27A | Amino Acid at Kabat 27B | Amino Acid at Kabat 27C |
|---|---|---|---|
| CPX-006 | N | V | S |
| CPX-008 | Q | V | S |
| CPX-009 | A | V | S |
| CPX-011 | N | V | A |
| CPX-012 | Q | V | S |
| CPX-014 | D | V | S |

Figure 4:
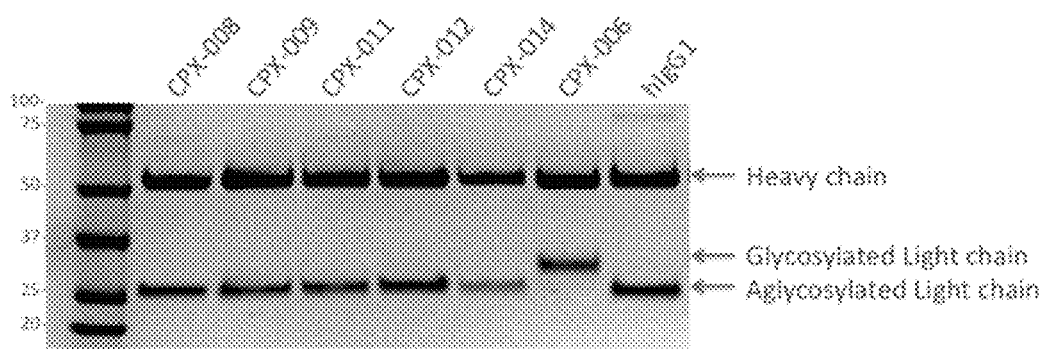
FIG. 4: Amino Acid Substitutions at Kabat Positions 27A or 27C Eliminate N-linked Glycosylation.

In FIG. 4 plasmids encoding light chains with the indicated amino acid substitutions were cotransfected with CPX-006 heavy chain (SEQ ID NO:9) into 293 cells. Antibody was purified from the cell culture media using Protein A chromatography. Purified antibodies were analyzed by SDS-PAGE under reducing conditions. hIgG1 was obtained from a commercial source and serves as a reference for the molecular weight of aglycosylated light chain (~25 kDa). CPX-006 light chain is glycosylated and runs slightly slower in SDS-PAGE with a molecular weight of ~30 kDa. CPX-008, CPX-009, CPX-011 CPX-012, and CPX-014 are aglycosylated due to substitutions made to eliminate the NXS motif for N-linked glycosylation.

Figure 5:
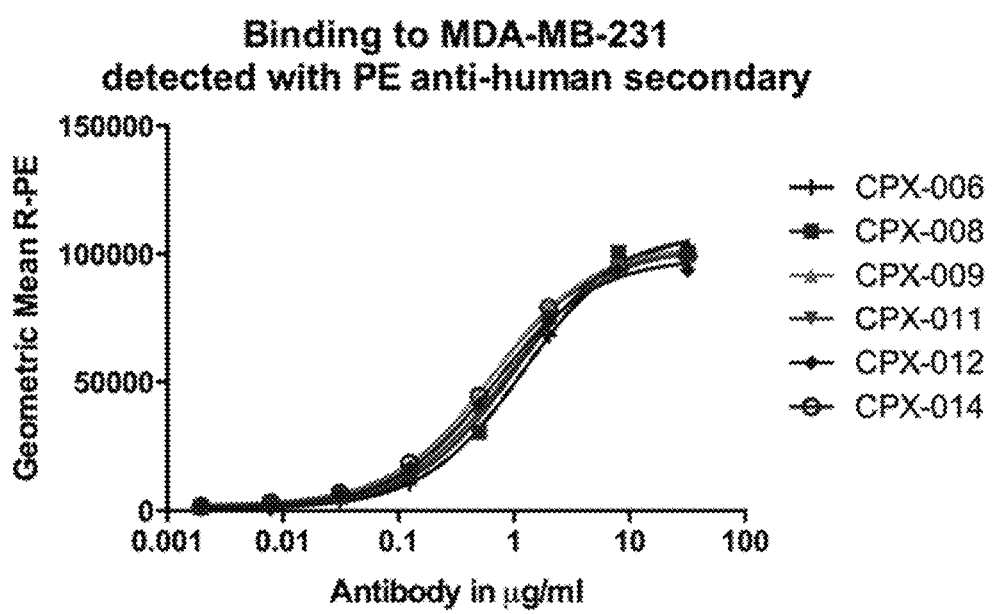
FIG. 5: Aglycosylated anti-CD73 Antibodies Bind to Cellular CD73 with Similar Potency as Glycosylated Antibody.

In FIG. 5 binding of CPX-006 (glycosylated) or aglycosylated derivatives was assessed by flow cytometry. MDA-MB-231, a human breast cancer cell line, was incubated with the indicated antibodies over a range of concentrations. Antibody binding was detected with PE anti-human secondary and flow cytometry analysis.

Figure 6:
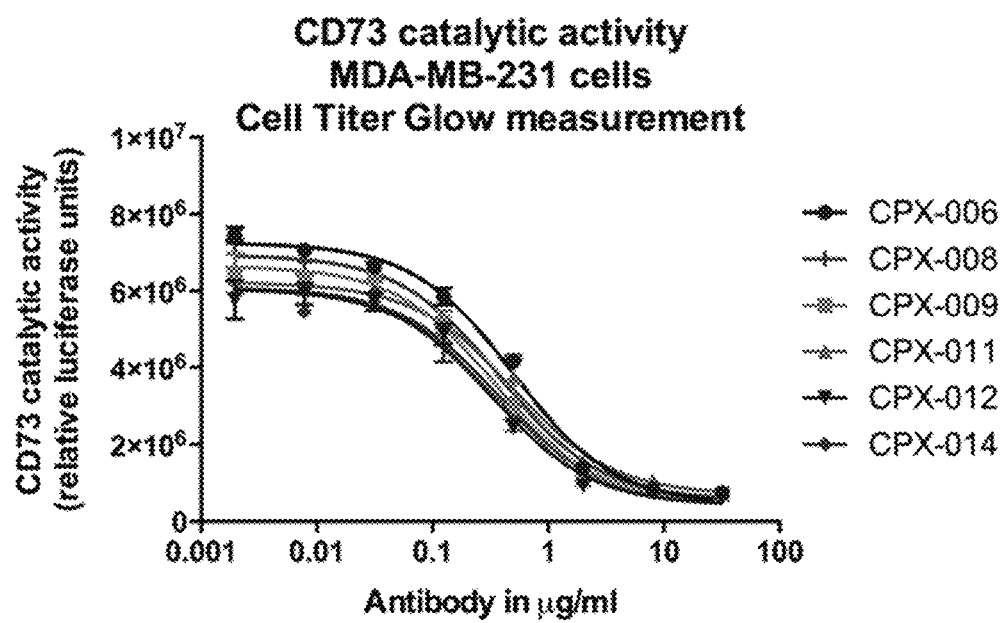
FIG. 6: Aglycosylated anti-CD73 Antibodies Inhibit CD73 Activity with Similar Potency to Glycosylated Antibody.

In FIG. 6 MDA-MB-231, a human breast cancer cell line, was incubated with the indicated antibodies over a range of concentrations. CD73 activity was measured as described in PMID: 22522649.

In FIG. 7, human PBMCs from 2 representative donors were labeled with CellTrace™ Violet, stimulated with anti-CD3 and anti-CD28 antibodies, and cultured in the presence of 3 mM AMP with either CPX006 (glycosylated antibody), CPX008 (aglycosylated antibody), or hIgG1 (isotype control) for 4 days. Proliferation of CD3+ cells was assessed by CellTrace™ Violet dilution using flow cytometry. Cell-Trace™ Violet Dim cells are CD3+ cells that have undergone two or more rounds of CellTrace™ Violet dilution and are plotted as a proportion of the total CD3+ population. Tables 2 and 3 show the EC50 for CPX006, hIgG1, and CPX008 measured for donors 1 and 2 of FIG. 7, respectively.

TABLE 2

EC50 for CPX006, hIgG1, and CPX008 as measured for donor 1 of FIG. 7.

|  | CPX006 | hIgG1 | CPX008 |
| --- | --- | --- | --- |
| EC50 | 42.55 | 277597492 | 42.7 |

TABLE 3

EC50 for CPX006, hIgG1, and CPX008 measured for donor 2 of FIG. 7.

|  | CPX006 | hIgG1 | CPX008 |
| --- | --- | --- | --- |
| EC50 | 61.6 | 97.29 | 49.86 |

Informal Sequence Listing

```
CDR L1: RASKNVSTSGYSYMH (SEQ ID NO: 1)

CDR L2: LASNLES (SEQ ID NO: 2)

CDR L3: QHSRELPFT (SEQ ID NO: 3)

CDR H1: GYTFTSYWIT (SEQ ID NO: 4)

CDR H2: PGSGNTNYNEKFKT (SEQ ID NO: 5)

CDR H3: EGGLTTEDY (SEQ ID NO: 6)

BAP094-hum06-LC, CPX-005 LC SEQ ID NO: 7:
AIQLTQSPSSLSASVGDRVTITCRASKNVSTSGYSYMHWYQQKPGQAPRLLIYLASNLES
GVPSRFSGSGSGTDFTFTISSLEAEDAATYYCQHSRELPFTFGQGTKVEIK BAP094-hum07-LC, CPX-006 LC SEQ ID NO: 8:
EIVLTQSPATLSLSPGERATLSCRASKNVSTSGYSYMHWYQQKPGQAPRLLIYLASNLES
GIPPRFSGSGYGTDFTLTINNIESEDAAYYFCQHSRELPFTFGQGTKVEIK BAP094-hum06-HC, CPX-005, CPX-006 HC (SEQ ID NO: 9):
QVQLVQSGAEVEKPGASVKVSCKASGYTFTSYWITWVRQAPGQGLEWMGDIYPGSGN
TNYNEKFKTRVTITADKSTSTAYMELSSLRSEDTAVYYCAKEGGLTTEDYALDWGQG
TLVTV BAP094-hum06-LC, CPX-005 SEQ ID NO: 10:
GCCATCCAGTTGACCCAGTCTCCATCCTCCCTGTCTGCATCTGTAGGAGACAGAGTC
ACCATCACTTGCAGGGCCAGCAAAAATGTCAGTACATCTGGCTATAGTTATATGCAC
TGGTACCAGCAGAAACCTGGCCAGGCTCCCAGGCTCCTCATCTATCTTGCATCCAAC
CTAGAATCTGGGGTCCCCTCGAGGTTCAGTGGCAGTGGATCTGGGACAGATTTCACC
TTTACCATCAGTAGCCTGGAAGCTGAAGATGCTGCAACATATTACTGTCAGCACAGT
AGGGAGCTTCCATTCACGTTCGGCCAAGGGACCAAGGTGGAAATCAAA BAP094-hum07-LC, CPX-006, SEQ ID NO: 11:
GAAATTGTGTTGACACAGTCTCCAGCCACCCTGTCTTTGTCTCCAGGGGAAAGAGCC
ACCCTCTCCTGCAGGGCCAGCAAAAATGTCAGTACATCTGGCTATAGTTATATGCAC
TGGTACCAGCAGAAACCTGGCCAGGCTCCCAGGCTCCTCATCTATCTTGCATCCAAC
CTAGAATCTGGGATCCCACCTCGATTCAGTGGCAGCGGGTATGGAACAGATTTTACC
CTCACAATTAATAACATAGAATCTGAGGATGCTGCATATTACTTCTGTCAGCACAGT
AGGGAGCTTCCATTCACGTTCGGCCAAGGGACCAAGGTGGAAATCAAA BAP094-hum06-HC, CPX-005, CPX-006 SEQ ID NO: 12:
CAGGTTCAGCTGGTGCAGTCTGGAGCTGAGGTGGAGAAGCCTGGGGCCTCAGTGAA
GGTCTCCTGCAAGGCTTCTGGCTACACCTTCACCAGCTACTGGATAACCTGGGTGCG
ACAGGCCCCTGGACAAGGGCTTGAGTGGATGGGTGATATTTATCCTGGTAGTGGTAA
TACTAACTACAATGAGAAGTTCAAGACCAGAGTCACGATTACCGCGGACAAATCCA
CGAGCACAGCCTACATGGAGCTGAGCAGCCTGAGATCTGAGGACACGGCCGTGTAT
TACTGTGCAAAAGAGGGAGGTCTTACTACGGAGGATTATGCTTTGGACTACTGGGGC
CAGGGAACGCTGGTCACCGTCAGCTCA
```

-continued

CPX-006 Light Chain (variable region in bold) SEQ ID NO: 13
EIVLTQSPATLSLSPGERATLSCRASKNVSTSGYSYMHWYQQKPGQAPRLLIYLASN
LESGIPPRFSGSGYGTDFTLTINNIESEDAAYYFCQHSRELPFTFGQGTKVEIKRTVA
APSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC CPX-006 Heavy Chain (variable region in bold) SEQ ID NO: 14
QVQLVQSGAEVEKPGASVKVSCKASGYTFTSYWITWVRQAPGQGLEWMGDIYPG
SGNTNYNEKFKTRVTITADKSTSTAYMELSSLRSEDTAVYYCAKEGGLTTEDYALD
YWGQGTLVTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKKVEPKSCDKT
HTCPPCPAPELLGGPSVFLFPPKPKDTLMISRTPEVTCVVVDVSHEDPEVKFNWYVDGV
EVHNAKTKPREEQYQSTYRVVSVLTVLHQDWLNGKEYKCKVSNKALPAPIEKTISKAK
GQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK CPX-005 Light Chain (variable region in bold) SEQ ID NO: 15
AIQLTQSPSSLSASVGDRVTITCRASKNVSTSGYSYMHWYQQKPGQAPRLLIYLASN
LESGVPSRFSGSGSGTDFTFTISSLEAEDAATYYCQHSRELPFTFGQGTKVEIKRTVA
APSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC CPX-005 Heavy Chain (variable region in bold) SEQ ID NO: 16
QVQLVQSGAEVEKPGASVKVSCKASGYTFTSYWITWVRQAPGQGLEWMGDIYPG
SGNTNYNEKFKTRVTITADKSTSTAYMELSSLRSEDTAVYYCAKEGGLTTEDYALD
YWGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVEPKSC
DKTHTCPPCPAPELLGGPSVFLFPPKPKDTLMISRTPEVTCVVVDVSHEDPEVKFNWYV
DGVEVHNAKTKPREEQYQSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK 1E9-mIgG3 light chain variable region SEQ ID NO: 17
DIVLTQSPASLAVSLGQRATISCRASKNVSTSGYSYMHWYQQKPGQPPKLLIYLASNLES
GVPTRFSGSGSGTDFTLNIHPVEEEDAATYYCQHSRELPFTFGSGTKLEIK 1E9-mIgG3 heavy chain variable region SEQ ID NO: 18
QVQLQQPGAELVKPGASVKMSCKASGYTFTSYWITWVKQRPGQGLEWIGDIYPGSGNT
NYNEKFKTKATLTVDTSSSTAYMQLSSLTSEDSAVYYCAKEGGLTTEDYALDYWGQGT
LVTVSS CPX-008 LC variable region SEQ ID NO: 19
EIVLTQSPATLSLSPGERATLSCRASKQVSTSGYSYMHWYQQKPGQAPRLLIYLASNLES
GIPPRFSGSGYGTDFTLTINNIESEDAAYYFCQHSRELPFTFGQGTKVEIK CPX-009 LC variable region SEQ ID NO: 20
EIVLTQSPATLSLSPGERATLSCRASKAVSTSGYSYMHWYQQKPGQAPRLLIYLASNLES
GIPPRFSGSGYGTDFTLTINNIESEDAAYYFCQHSRELPFTFGQGTKVEIK CPX-011 LC variable region SEQ ID NO: 21
EIVLTQSPATLSLSPGERATLSCRASKNVATSGYSYMHWYQQKPGQAPRLLIYLASNLES
GIPPRFSGSGYGTDFTLTINNIESEDAAYYFCQHSRELPFTFGQGTKVEIK CPX-012 LC variable region SEQ ID NO: 22
AIQLTQSPSSLSASVGDRVTITCRASKQVSTSGYSYMHWYQQKPGQAPRLLIYLASNLES
GVPSRFSGSGSGTDFTFTISSLEAEDAATYYCQHSRELPFTFGQGTKVEIK CPX-014 LC variable region SEQ ID NO: 23
EIVLTQSPATLSLSPGERATLSCRASKDVSTSGYSYMHWYQQKPGQAPRLLIYLASNLES
GIPPRFSGSGYGTDFTLTINNIESEDAAYYFCQHSRELPFTFGQGTKVEIK WBP2094-HC codon optimized (SEQ ID NO: 24)
ATGGGGTCAACCGCCATCCTTGGCCTCCTCCTGGCTGTTCTCCAAGGAGTCTGTGCC
CAGGTTCAGCTGGTGCAGTCTGGAGCTGAGGTGGAGAAGCCTGGGGGCCTCAGTGAA
GGTCTCCTGCAAGGCTTCTGGCTACACCTTCACCAGCTACTGGATAACCTGGGTGCG
ACAGGCCCCTGGACAAGGGCTTGAGTGGATGGGTGATATTTATCCTGGTAGTGGTAA
TACTAACTACAATGAGAAGTTCAAGACCAGAGTCACGATTACCGCGGACAAATCCA
CGAGCACAGCCTACATGGAGCTGAGCAGCCTGAGATCTGAGGACACAGCCGTGTAT
TACTGTGCAAAAGAGGGAGGTCTTACTACGGAGGATTATGCTTTGGACTACTGGGGC
CAGGGAACGCTGGTCACCGTCAGCTCAGCTAGCACCAAGGGCCCATCCGTCTTCCCC
CTGGCGCCCTGCTCCAGGTCTACCTCCGAGTCTACAGCCGCCCTGGGCTGCCTGGTC
AAGGACTACTTCCCCGAACCGGTGACGGTGTCGTGGAACTCAGGCGCCCTGACCTCT
GGCGTGCACACCTTCCCGGCTGTCCTACAGTCCTCAGGACTCTACTCCCTCTCTTCTG
TGGTGACCGTGCCCTCCTCTTCTTTGGGCACGAAGACCTACACCTGCAACGTAGATC
ACAAGCCCTCTAACACCAAGGTGGACAAGAGAGTTGAGTCCAAATATGGTCCCCCA
TGCCCACCATGCCCAGCACCTGAGTTCCTGGGGGGACCATCCTTCTTCCTGTTCCCC
CCAAAACCCAAGGACACTCTCATGATCTCCCGGACCCCTGAGGTCACGTGCGTGGTG
GTGGACGTGTCTCAGGAAGACCCCGAGGTCCAGTTCAACTGGTACGTGGATGGCGT
GGAGGTGCATAATGCCAAGACAAAGCCGCGGGAGGAGCAGTTCAACTCTACGTACC
GTGTGGTCTCTGTCCTCACCGTCCTGCACCAGGACTGGCTGAACGGCAAGGAGTACA
AGTGCAAGGTCTCCAACAAAGGCCTCCCGTCCTCCATCGAGAAAACCATCTCCAAA

```
-continued
GCCAAAGGGCAGCCCCGAGAGCCACAGGTGTACACCCTGCCCCCATCCCAGGAGGA
GATGACCAAGAACCAGGTCTCTCTGACCTGCCTGGTCAAAGGCTTCTACCCCTCTGA
CATCGCCGTGGAGTGGGAGTCTAATGGGCAGCCGGAGAACAACTACAAGACCACGC
CTCCCGTGCTGGACTCCGACGGCTCCTTCTTCCTCTACTCTAGGCTAACCGTGGACA
AGTCTAGGTGGCAGGAGGGGAATGTCTTCTCATGCTCCGTGATGCATGAGGCTCTGC
ACAACCACTACACACAGAAGTCTCTCTCCCTGTCTCTGGGTAAATGA WBP2094-LC codon optimized (SEQ ID NO: 25)
ATGGAAGCCCCAGCGCAGCTTCTCTTCCTCCTGCTACTCTGGCTCCCAGATACCACC
GGAGAAATTGTGTTGACACAGTCTCCAGCCACCCTGTCTTTGTCTCCAGGGGAAAGA
GCCACCCTCTCCTGCAGGGCCAGCAAACAGGTCAGTACATCTGGCTATAGTTATATG
CACTGGTACCAGCAGAAACCTGGCCAGGCTCCCAGGCTCCTCATCTATCTTGCATCC
AACCTAGAATCTGGGATCCCACCTCGATTCAGTGGCAGCGGGTATGGAACAGATTTT
ACCCTCACAATTAATAACATAGAATCTGAGGATGCTGCATATTACTTCTGTCAGCAC
AGTAGGGAGCTTCCATTCACGTTCGGCCAAGGGACCAAGGTGGAAATCAAACGTAC
GGTGGCTGCACCATCTGTCTTCATCTTCCCGCCATCTGATGAGCAGTTGAAATCTGG
AACTGCCTCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCACAGAGC
AGGACTCTAAGGACTCTACCTACTCTCTCTTCTTACCCTGACGCTGTCTAAAGCAG
ACTACGAGAAACACAAAGTCTACGCCTGCGAAGTCACCCATCAGGGCCTGTCTTCG
CCCGTCACAAAGTCTTTCAACAGGGGAGAGTGTTGA WBP2094-HC (protein) SEQ ID NO: 26
MGSTAILGLLLAVLQGVCAQVQLVQSGAEVEKPGASVKVSCKASGYTFTSYWITWVRQ
APGQGLEWMGDIYPGSGNTNYNEKFKTRVTITADKSTSTAYMELSSLRSEDTAVYYCA
KEGGLTTEDYALDYWGQGTLVTVSSASTKGPSVFPLAPCSRSTSESTAALGCLVKDYFP
EPVTVSWNSGALTSGVHTFPAVLQSSGLYSLSSVVTVPSSSLGTKTYTCNVDHKPSNTK
VDKRVESKYGPPCPPCPAPEFLGGPSVFLFPPKPKDTLMISRTPEVTCVVVDVSQEDPEV
QFNWYVDGVEVHNAKTKPREEQFNSTYRVVSVLTVLHQDWLNGKEYKCKVSNKGLPS
SIEKTISKAKGQPREPQVYTLPPSQEEMTKNQVSLTCLVKGFYPSDIAVEWESNGQPENN
YKTTPPVLDSDGSFFLYSRLTVDKSRWQEGNVFSCSVMHEALHNHYTQKSLSLSLGK WBP2094-LC (protein) SEQ ID NO: 27
MEAPAQLLFLLLLWLPDTTGEIVLTQSPATLSLSPGERATLSCRASKQVSTSGYSYMHW
YQQKPGQAPRLLIYLASNLESGIPPRFSGSGYGTDFTLTINNIESEDAAYYFCQHSRELPFT
FGQGTKVEIKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSFNRGEC Nucleic acid sequence of CPX-008, light chain SEQ ID NO: 28
GAAATTGTGTTGACACAGTCTCCAGCCACCCTGTCTTTGTCTCCAGGGGAAAGAGCC
ACCCTCTCCTGCAGGGCCAGCAAACAGGTCAGTACATCTGGCTATAGTTATATGCAC
TGGTACCAGCAGAAACCTGGCCAGGCTCCCAGGCTCCTCATCTATCTTGCATCCAAC
CTAGAATCTGGGATCCCACCTCGATTCAGTGGCAGCGGGTATGGAACAGATTTTACC
CTCACAATTAATAACATAGAATCTGAGGATGCTGCATATTACTTCTGTCAGCACAGT
AGGGAGCTTCCATTCACGTTCGGCCAAGGGACCAAGGTGGAAATCAAACGTACGGT
GGCTGCACCATCTGTCTTCATCTTCCCGCCATCTGATGAGCAGTTGAAATCTGGAAC
TGCCTCTGTTGTGTGCCTGCTGAATAACTTCTATCCCAGAGAGGCCAAAGTACAGTG
GAAGGTGGATAACGCCCTCCAATCGGGTAACTCCCAGGAGAGTGTCACAGAGCAGG
ACAGCAAGGACAGCACCTACAGCCTCAGCAGCACCCTGACGCTGAGCAAAGCAGAC
TACGAGAAACACAAAGTCTACGCCTGCGAAGTCACCCATCAGGGCCTGAGCTCGCC
CGTCACAAAGAGCTTCAACAGGGGAGAGTGT
```

Embodiments

Embodiment 1. An anti-CD73 antibody comprising: (i) a CDR L1 of SEQ ID NO:1; and (ii) an amino acid substitution selected from the group consisting of: (a) any amino acid other than asparagine at a position corresponding to Kabat position 27A of SEQ ID NO:1; (b) any amino acid other than valine at a position corresponding to Kabat position 27B of SEQ ID NO:1; or (c) any amino acid other than serine at a position corresponding to Kabat position 27C of SEQ ID NO:1.

Embodiment 2. The anti-CD73 antibody of embodiment 1, wherein said amino acid is an unnatural amino acid.

Embodiment 3. The anti-CD73 antibody of embodiment 1 or 2, wherein said amino acid other than asparagine is glycine, an alanine, a leucine, a methionine, a phenylalanine, a tryptophan, a lysine, a glutamine, a glutamic acid, a serine, a proline, a valine, an isoleucine, a cysteine, a tyrosine, a histidine, an arginine, an aspartic acid or a threonine at a position corresponding to Kabat position 27A.

Embodiment 4. The anti-CD73 antibody of one of embodiments 1-3, wherein said amino acid other than valine is a glycine, an alanine, a leucine, a methionine, a phenylalanine, a tryptophan, a lysine, a glutamine, a glutamic acid, a serine, a proline, an isoleucine, a cysteine, a tyrosine, a histidine, an arginine, an asparagine, an aspartic acid or a threonine at a position corresponding to Kabat position 27B.

Embodiment 5. The anti-CD73 antibody of one of embodiments 1-4, wherein said amino acid other than serine is a glycine, an alanine, a leucine, a methionine, a phenylalanine, a tryptophan, a lysine, a glutamine, a glutamic acid, a proline, a valine, an isoleucine, a cysteine, a tyrosine, a histidine, an arginine, an asparagine, an aspartic acid or a threonine at a position corresponding to Kabat position 27C.

Embodiment 6. The anti-CD73 antibody of one of embodiments 1-5, wherein said amino acid other than asparagine is an alanine, a glycine, a glutamine, an aspartic acid or an arginine at a position corresponding to Kabat position 27A.

Embodiment 7. The anti-CD73 antibody of one of embodiments 1-6, wherein said amino acid other than serine is an alanine at a position corresponding to Kabat position 27C.

Embodiment 8. The anti-CD73 antibody of one of embodiments 1-6, wherein said amino acid other than asparagine is a glutamine at a position corresponding to Kabat position 27A.

Embodiment 9. The anti-CD73 antibody of embodiment 8, wherein said anti-CD73 antibody comprises a valine at a position corresponding to Kabat position 27B.

Embodiment 10. The anti-CD73 antibody of embodiment 10, wherein said anti-CD73 antibody comprises serine at a position corresponding to Kabat position 27C.

Embodiment 11. The anti-CD73 antibody of one of embodiments 1-6, wherein said amino acid other than valine is a proline at a position corresponding to Kabat position 27B.

Embodiment 12. The anti-CD73 antibody of embodiment 11, wherein said anti-CD73 antibody comprises an asparagine at a position corresponding to Kabat position 27A.

Embodiment 13. The anti-CD73 antibody of embodiment 12, wherein said anti-CD73 antibody comprises a serine at a position corresponding to Kabat position 27C.

Embodiment 14. The anti-CD73 antibody of one of embodiments 1-13, further comprising a CDR L2 as set forth in SEQ ID NO:2.

Embodiment 15. The anti-CD73 antibody of one of embodiments 1-14, further comprising a CDR L3 as set forth in SEQ ID NO:3.

Embodiment 16. The anti-CD73 antibody of one of embodiments 1-15, further comprising a CDR H1 as set forth in SEQ ID NO:4.

Embodiment 17. The anti-CD73 antibody of one of embodiments 1-16, further comprising a CDR H2 as set forth in SEQ ID NO:5.

Embodiment 18. The anti-CD73 antibody of one of embodiments 1-17, further comprising a CDR H3 as set forth in SEQ ID NO:6.

Embodiment 19. The anti-CD73 antibody of one of embodiments 1-18, comprising a sequence of SEQ ID NO:26.

Embodiment 20. The anti-CD73 antibody of one of embodiments 1-19, comprising a sequence of SEQ ID NO:27.

Embodiment 21. The anti-CD73 antibody of one of embodiments 1-20, wherein said antibody is a chimeric antibody.

Embodiment 22. The anti-CD73 antibody of one of embodiments 1-20, wherein said antibody is a humanized antibody.

Embodiment 23. The anti-CD73 antibody of one of embodiments 1-21, wherein said antibody is an IgG.

Embodiment 24. The anti-CD73 antibody of one of embodiments 1-23, wherein said antibody is an IgG1.

Embodiment 25. The anti-CD73 antibody of one of embodiments 1-23, wherein said antibody is an IgG4.

Embodiment 26. The anti-CD73 antibody of one of embodiments 1-21, wherein said antibody is a Fab' fragment.

Embodiment 27. The anti-CD73 antibody of one of embodiments 1-21, wherein said antibody is a single chain antibody (scFv).

Embodiment 28. The anti-CD73 antibody of one of embodiments 1-27, wherein said antibody is capable of binding a CD73 antigen with an equilibrium dissociation constant ($K_D$) from about 0.5 to about 25 nM.

Embodiment 29. The anti-CD73 antibody of one of embodiments 1-28, wherein said antibody is capable of binding a CD73 antigen at a pH of less than about 7.5.

Embodiment 30. The anti-CD73 antibody of one of embodiment 1-29, wherein said antibody is capable of binding a CD73 antigen at a pH from about 6.0 to about 7.0.

Embodiment 31. The anti-CD73 antibody of one of embodiments 1-30, wherein said antibody is capable of binding a CD73 antigen at a pH of about 6.3.

Embodiment 32. The anti-CD73 antibody of one of embodiments 1-31, further comprising a glutamine at a position corresponding to Kabat position 297.

Embodiment 33. The anti-CD73 antibody of one of embodiments 1-32, bound to a CD73 antigen.

Embodiment 34. The anti-CD73 antibody of embodiment 33, wherein said CD73 antigen forms part of a cell.

Embodiment 35. The anti-CD73 antibody of embodiment 34, wherein said cell is a lymphoid cell.

Embodiment 36. The anti-CD73 antibody of embodiment 34 or 35, wherein said cell is a T cell.

Embodiment 37. The anti-CD73 antibody of embodiment 34, wherein said cell is a cancer cell.

Embodiment 38. An isolated nucleic acid encoding an anti-CD73 antibody of one of embodiments 1-37.

Embodiment 39. The isolated nucleic acid of embodiment 38, wherein said nucleic acid comprises the sequence of SEQ ID NO:24 or SEQ ID NO:25.

Embodiment 40. The isolated nucleic acid of embodiment 38, wherein said nucleic acid comprises the sequence of SEQ ID NO:24.

Embodiment 41. The isolated nucleic acid of embodiment 38, wherein said nucleic acid comprises the sequence of SEQ ID NO:25.

Embodiment 42. The isolated nucleic acid of any one of embodiments 38-41, wherein said nucleic acid forms part of a cell.

Embodiment 43. A pharmaceutical composition comprising a therapeutically effective amount of an anti-CD73 antibody of one of embodiments 1-37 and a pharmaceutically acceptable excipient.

Embodiment 44. A method of treating cancer in a subject in need thereof, said method comprising administering to said subject a therapeutically effective amount of an anti-CD73 antibody of one of embodiments 1-37, thereby treating cancer in said subject.

What is claimed is:

1. An anti-CD73 antibody comprising:
   (i) a light chain variable domain comprising a CDR L1 comprising the amino acid sequence of SEQ ID NO:1, but for the replacement of the asparagine residue therein with an amino acid residue selected from alanine, glycine, glutamine, and aspartic acid, a CDR L2 comprising the amino acid sequence of SEQ ID NO:2 and a CDR L3 comprising the amino acid sequence of SEQ ID NO:3; and
   (ii) a heavy chain variable domain comprising a CDR H1 comprising the amino acid sequence of SEQ ID NO:4, a CDR H2 comprising the amino acid sequence of SEQ ID NO:5 and a CDR H3 comprising the amino acid sequence of SEQ ID NO:6.

2. The anti-CD73 antibody of claim 1, wherein said CDR L1 is modified by the replacement of the asparagine residue therein with glutamine.

3. The anti-CD73 antibody of claim 1, wherein the heavy chain variable domain comprises the amino acid sequence of SEQ ID NO:26.

4. The anti-CD73 antibody of claim 2, wherein the light chain variable domain comprises the amino acid sequence of SEQ ID NO:27.

5. The anti-CD73 antibody of claim 1, wherein said antibody is a chimeric antibody or a humanized antibody.

6. The anti-CD73 antibody of claim 1, wherein said antibody is a Fab' fragment or a single chain antibody (scFv).

7. The anti-CD73 antibody of claim 1, wherein said antibody is capable of binding a CD73 antigen with an equilibrium dissociation constant (KD) from about 0.5 to about 25 nM.

8. The anti-CD73 antibody of claim 1, wherein said antibody is capable of binding a CD73 antigen at a pH from about 6.0 to about 7.0.

9. An isolated nucleic acid encoding an anti-CD73 antibody of claim 1.

10. The isolated nucleic acid of claim 9, wherein said nucleic acid forms part of a cell.

11. A pharmaceutical composition comprising an anti-CD73 antibody of claim 1 and a pharmaceutically acceptable excipient.

* * * * *